(12) United States Patent
Sacks et al.

(10) Patent No.: US 12,396,886 B2
(45) Date of Patent: Aug. 26, 2025

(54) AUTOMATED CAPSULOTOMY

(71) Applicant: BELKIN VISION LTD., Yavne (IL)

(72) Inventors: Zachary Shane Sacks, Modiin (IL); Michael Belkin, Givat Shmu'el (IL)

(73) Assignee: Belkin Vision Ltd., Yavne (IL)

( * ) Notice: Subject to any disclaimer, the term of this patent is extended or adjusted under 35 U.S.C. 154(b) by 268 days.

(21) Appl. No.: 17/926,633

(22) PCT Filed: May 16, 2021

(86) PCT No.: PCT/IB2021/054187
§ 371 (c)(1),
(2) Date: Nov. 21, 2022

(87) PCT Pub. No.: WO2022/018525
PCT Pub. Date: Jan. 27, 2022

(65) Prior Publication Data
US 2023/0201034 A1    Jun. 29, 2023

Related U.S. Application Data

(60) Provisional application No. 63/053,650, filed on Jul. 19, 2020.

(51) Int. Cl.
*A61F 9/008*    (2006.01)
(52) U.S. Cl.
CPC .... *A61F 9/008* (2013.01); *A61F 2009/00844* (2013.01); *A61F 2009/0087* (2013.01);
(Continued)

(58) Field of Classification Search
CPC ............ A61F 9/008; A61F 2009/00844; A61F 2009/0087; A61F 2009/00889; A61F 2009/00897
(Continued)

(56) References Cited

U.S. PATENT DOCUMENTS 2,635,502 A    4/1953    Richards
3,594,072 A    7/1971    Feather
(Continued)

FOREIGN PATENT DOCUMENTS

AU    2015210430 A1    9/2015
AU    2015315113 B2    3/2016
(Continued)

OTHER PUBLICATIONS

CN Application # 2020800163407 Office Action dated Feb. 4, 2023.
(Continued)

*Primary Examiner* — Aaron F Roane
(74) *Attorney, Agent, or Firm* — Meitar Patents Ltd.; Daniel Kligler

(57) ABSTRACT

A system (20) includes a radiation source (48) and a controller (44). The controller is configured to define a treatment zone (88) on a capsule (86) of an eye (25) of a subject (22), and to form an opening (96) in the capsule, subsequently to defining the treatment zone, by irradiating multiple target regions (94) within the treatment zone in an iterative process that includes, during each one of multiple iterations of the process, acquiring an image (98) of at least part of the capsule, designating one of the target regions based on the acquired image, and causing the radiation source to irradiate the designated target region. Other embodiments are also described.

29 Claims, 7 Drawing Sheets

(52) U.S. Cl.
CPC .............. *A61F 2009/00889* (2013.01); *A61F 2009/00897* (2013.01)

(58) Field of Classification Search
USPC .......................................................... 606/4
See application file for complete search history.

(56) References Cited

U.S. PATENT DOCUMENTS

| | | |
|---|---|---|
| 4,587,257 A | 5/1986 | DeSantis et al. |
| 4,641,349 A | 2/1987 | Flom et al. |
| 4,718,418 A | 1/1988 | L'Esperance |
| 4,848,894 A | 7/1989 | Buser et al. |
| 4,941,093 A | 7/1990 | Marshall et al. |
| 4,966,452 A | 10/1990 | Shields et al. |
| 5,049,147 A | 9/1991 | Danon |
| 5,123,902 A | 6/1992 | Muller et al. |
| 5,141,506 A | 8/1992 | York |
| 5,151,909 A | 9/1992 | Davenport et al. |
| 5,152,760 A | 10/1992 | Latina |
| 5,370,641 A | 12/1994 | O'Donnell, Jr. |
| 5,422,899 A | 6/1995 | Freiberg et al. |
| 5,479,222 A | 12/1995 | Volk et al. |
| 5,537,164 A | 7/1996 | Smith |
| 5,549,596 A | 8/1996 | Latina |
| 5,598,007 A | 1/1997 | Bunce et al. |
| 5,786,883 A | 7/1998 | Miller et al. |
| 5,865,830 A | 2/1999 | Parel et al. |
| 5,982,789 A | 11/1999 | Marshall et al. |
| 6,027,216 A | 2/2000 | Guyton et al. |
| 6,030,376 A | 2/2000 | Arashima et al. |
| 6,033,396 A | 3/2000 | Huang et al. |
| 6,059,772 A | 5/2000 | Hsia et al. |
| 6,096,029 A | 8/2000 | O'Donnell, Jr. |
| 6,099,521 A | 8/2000 | Shadduck |
| 6,099,522 A | 8/2000 | Knopp et al. |
| 6,146,375 A | 11/2000 | Juhasz et al. |
| 6,159,202 A | 12/2000 | Sumiya et al. |
| 6,210,399 B1 | 4/2001 | Parel et al. |
| 6,258,082 B1 | 7/2001 | Lin |
| 6,263,879 B1 | 7/2001 | Lin |
| 6,267,752 B1 | 7/2001 | Svetliza |
| 6,267,756 B1 | 7/2001 | Feuerstein et al. |
| 6,286,960 B1 | 9/2001 | Tomita |
| 6,319,274 B1 | 11/2001 | Shadduck |
| 6,325,792 B1 | 12/2001 | Swinger et al. |
| 6,414,980 B1 | 7/2002 | Wang et al. |
| 6,454,763 B1 | 9/2002 | Motter et al. |
| 6,514,241 B1 | 2/2003 | Hsia et al. |
| 6,530,916 B1 | 3/2003 | Shimmick |
| 6,569,104 B2 | 5/2003 | Ono et al. |
| 6,585,723 B1 | 7/2003 | Sumiya |
| 6,673,062 B2 | 1/2004 | Yee et al. |
| 6,676,655 B2 | 1/2004 | McDaniel |
| 6,685,317 B2 | 2/2004 | Su et al. |
| 6,698,886 B2 | 3/2004 | Pollack et al. |
| 6,736,806 B2 | 5/2004 | Ruiz et al. |
| 6,761,713 B2 | 7/2004 | Teichmann |
| 6,899,707 B2 | 5/2005 | Scholler et al. |
| 6,942,656 B2 | 9/2005 | Pawlowski et al. |
| 6,948,815 B2 | 9/2005 | Neuberger |
| 6,979,328 B2 | 12/2005 | Baerveldt et al. |
| 7,027,233 B2 | 4/2006 | Goldstein et al. |
| 7,252,661 B2 | 8/2007 | Nguyen et al. |
| 7,282,046 B2 | 10/2007 | Simon |
| 7,353,829 B1 | 4/2008 | Wachter et al. |
| 7,371,230 B2 | 5/2008 | Webb et al. |
| 7,693,259 B2 | 4/2010 | Gertner |
| 7,792,249 B2 | 9/2010 | Gertner et al. |
| 8,004,764 B2 | 8/2011 | Artsyukhovich et al. |
| 8,048,065 B2 | 11/2011 | Grecu et al. |
| 8,109,635 B2 | 2/2012 | Allon et al. |
| 8,160,113 B2 | 4/2012 | Adams et al. |
| 8,403,921 B2 | 3/2013 | Palankar et al. |
| 8,442,185 B2 | 5/2013 | Gertner et al. |
| 8,465,478 B2 | 6/2013 | Frey et al. |
| 8,475,433 B2 | 7/2013 | Mrochen et al. |
| 8,545,020 B2 | 10/2013 | Liesfeld et al. |
| 8,568,393 B2 | 10/2013 | Palanker |
| 8,630,388 B2 | 1/2014 | Gertner et al. |
| 8,679,100 B2 | 3/2014 | Raksi et al. |
| 8,708,491 B2 | 4/2014 | Frey et al. |
| 8,709,029 B2 | 4/2014 | Griffis, III et al. |
| 8,771,261 B2 | 7/2014 | Andersen et al. |
| 8,811,657 B2 | 8/2014 | Teiwes et al. |
| 8,845,625 B2 | 9/2014 | Angeley et al. |
| 8,903,468 B2 | 12/2014 | Peyman |
| 8,920,407 B2 | 12/2014 | Raksi et al. |
| 8,939,965 B2 | 1/2015 | Liesfeld et al. |
| 8,968,279 B2 | 3/2015 | Arnoldussen |
| 8,995,618 B2 | 3/2015 | Gertner |
| 9,055,896 B2 | 6/2015 | Amthor et al. |
| 9,192,780 B2 | 11/2015 | McDaniel |
| 9,220,407 B2 | 12/2015 | Yam et al. |
| 9,351,878 B2 | 5/2016 | Muehlhoff et al. |
| 9,480,599 B2 | 11/2016 | Degani et al. |
| 9,495,743 B2 | 11/2016 | Angeley et al. |
| 9,504,609 B2 | 11/2016 | Kurtz |
| 9,532,712 B2 | 1/2017 | Liesfeld et al. |
| 9,622,911 B2 | 4/2017 | Rubinfeld et al. |
| 9,782,232 B1 | 10/2017 | Papac |
| 9,849,032 B2 | 12/2017 | Schuele et al. |
| 9,849,034 B2 | 12/2017 | Artsyukhovich et al. |
| 9,877,633 B2 | 1/2018 | Zhao et al. |
| 9,889,043 B2 | 2/2018 | Frey et al. |
| 9,968,483 B2 | 5/2018 | Takeda et al. |
| 10,022,457 B2 | 7/2018 | Peyman |
| 10,064,757 B2 | 9/2018 | Berlin |
| 10,143,590 B2 | 12/2018 | Dick et al. |
| 10,244,991 B2 | 4/2019 | Shademan et al. |
| 10,258,507 B2 | 4/2019 | Gonzalez et al. |
| 10,278,865 B2 | 5/2019 | Luttrull et al. |
| 10,299,961 B2 | 5/2019 | Luttrull et al. |
| 10,363,169 B2 | 7/2019 | Belkin et al. |
| 10,441,465 B2 | 10/2019 | Hart et al. |
| 10,449,091 B2 | 10/2019 | Angeley et al. |
| 10,456,209 B2 | 10/2019 | Peyman |
| 10,478,342 B2 | 11/2019 | Dick et al. |
| 10,524,656 B2 | 1/2020 | Wiltberger et al. |
| 10,617,564 B1 | 4/2020 | Andersen et al. |
| 10,684,449 B2 | 6/2020 | Curatu et al. |
| 10,702,416 B2 | 7/2020 | Belkin et al. |
| 10,849,789 B2 | 12/2020 | Dewey et al. |
| 10,925,768 B2 | 2/2021 | Charles |
| 11,406,536 B2 | 8/2022 | Schuele et al. |
| 2001/0027314 A1 | 10/2001 | Peyman |
| 2002/0013572 A1 | 1/2002 | Berlin |
| 2002/0013573 A1 | 1/2002 | Telfair et al. |
| 2002/0026179 A1 | 2/2002 | Toh |
| 2003/0179344 A1 | 9/2003 | Van de Velde |
| 2003/0225398 A1 | 12/2003 | Zepkin et al. |
| 2004/0039378 A1 | 2/2004 | Lin |
| 2004/0059321 A1 | 3/2004 | Knopp et al. |
| 2004/0196431 A1 | 10/2004 | Farberov |
| 2005/0096639 A1 | 5/2005 | Slatkine et al. |
| 2005/0107774 A1 | 5/2005 | Lin |
| 2005/0185138 A1 | 8/2005 | Wong et al. |
| 2005/0197655 A1 | 9/2005 | Telfair et al. |
| 2005/0254009 A1 | 11/2005 | Baker et al. |
| 2005/0286019 A1 | 12/2005 | Wiltberger et al. |
| 2005/0288745 A1 | 12/2005 | Andersen et al. |
| 2006/0100677 A1 | 5/2006 | Blumenkranz et al. |
| 2006/0176913 A1 | 8/2006 | Souhaite et al. |
| 2006/0195076 A1 | 8/2006 | Blumenkranz et al. |
| 2006/0224147 A1 | 10/2006 | Abe et al. |
| 2006/0265030 A1 | 11/2006 | McDaniel |
| 2007/0081166 A1 | 4/2007 | Brown et al. |
| 2007/0129709 A1 | 6/2007 | Andersen et al. |
| 2007/0159600 A1 | 7/2007 | Gil et al. |
| 2007/0213693 A1 | 9/2007 | Plunkett |
| 2008/0027418 A1 | 1/2008 | Berry |
| 2008/0089481 A1 | 4/2008 | Gertner |
| 2008/0108934 A1 | 5/2008 | Berlin et al. |
| 2008/0161781 A1 | 7/2008 | Mcardle et al. |
| 2008/0167642 A1 | 7/2008 | Palanker et al. |

(56) References Cited

U.S. PATENT DOCUMENTS

| | | |
|---|---|---|
| 2008/0204658 A1 | 8/2008 | Van Saarloos |
| 2008/0234667 A1 | 9/2008 | Lang et al. |
| 2008/0255546 A1 | 10/2008 | Orbachevski |
| 2009/0137993 A1 | 5/2009 | Kurtz |
| 2009/0157062 A1 | 6/2009 | Hauger et al. |
| 2009/0247997 A1 | 10/2009 | Watanabe et al. |
| 2010/0002837 A1 | 1/2010 | Gertner et al. |
| 2010/0057059 A1 | 3/2010 | Makino |
| 2010/0076419 A1 | 3/2010 | Chew et al. |
| 2010/0142767 A1 | 6/2010 | Fleming |
| 2010/0324543 A1 | 12/2010 | Kurtz et al. |
| 2011/0144627 A1 | 6/2011 | Smith et al. |
| 2011/0172649 A1 | 7/2011 | Schuele et al. |
| 2011/0190741 A1 | 8/2011 | Deisinger et al. |
| 2012/0016349 A1 | 1/2012 | Brownell |
| 2012/0050308 A1 | 3/2012 | Nakano et al. |
| 2012/0083772 A1 | 4/2012 | Rubinfeld et al. |
| 2012/0089134 A1 | 4/2012 | Horvath et al. |
| 2012/0259321 A1 | 10/2012 | Vera et al. |
| 2012/0283557 A1 | 11/2012 | Berlin |
| 2013/0103011 A1 | 4/2013 | Grant et al. |
| 2013/0123761 A1 | 5/2013 | Belkin et al. |
| 2013/0158530 A1 | 6/2013 | Goldshleger et al. |
| 2013/0204236 A1 | 8/2013 | Awdeh |
| 2013/0218145 A1 | 8/2013 | Belkin et al. |
| 2013/0289450 A1 | 10/2013 | Homer |
| 2013/0317570 A1 | 11/2013 | Luttrull et al. |
| 2014/0094785 A1 | 4/2014 | Charles |
| 2014/0114297 A1 | 4/2014 | Woodley et al. |
| 2014/0128731 A1 | 5/2014 | Gonzalez et al. |
| 2014/0128851 A1 | 5/2014 | Wysopal |
| 2014/0128852 A1 | 5/2014 | Gooding et al. |
| 2014/0135747 A1 | 5/2014 | Donitzky et al. |
| 2014/0135753 A1 | 5/2014 | Feklistov et al. |
| 2014/0276681 A1 | 9/2014 | Schuele et al. |
| 2014/0307077 A1 | 10/2014 | Prabhakar |
| 2015/0164635 A1 | 6/2015 | Renke |
| 2015/0190276 A1 | 7/2015 | Ha et al. |
| 2015/0223683 A1 | 8/2015 | Davidovics et al. |
| 2015/0266706 A1 | 9/2015 | Hashimoto |
| 2015/0272782 A1 | 10/2015 | Schuele et al. |
| 2015/0313759 A1 | 11/2015 | Vera et al. |
| 2016/0008169 A1 | 1/2016 | Yu |
| 2016/0008172 A1 | 1/2016 | Kahook |
| 2016/0008923 A1 | 1/2016 | Astle et al. |
| 2016/0067035 A1 | 3/2016 | Gontijo et al. |
| 2016/0067087 A1 | 3/2016 | Tedford et al. |
| 2016/0089232 A1 | 3/2016 | DeBoer et al. |
| 2016/0089269 A1 | 3/2016 | Horvath et al. |
| 2016/0095752 A1 | 4/2016 | Srinivasan et al. |
| 2016/0113816 A1 | 4/2016 | Herekar et al. |
| 2016/0346126 A1 | 12/2016 | Luttrull et al. |
| 2016/0354241 A1 | 12/2016 | Mordaunt et al. |
| 2016/0367399 A1 | 12/2016 | Goldshleger et al. |
| 2017/0000647 A1 | 1/2017 | Schuele et al. |
| 2017/0038284 A1 | 2/2017 | Nemati |
| 2017/0087014 A1 | 3/2017 | Potter, Jr. et al. |
| 2017/0112663 A1 | 4/2017 | Bareket et al. |
| 2017/0127938 A1 | 5/2017 | Izatt et al. |
| 2017/0184875 A1 | 6/2017 | Newman |
| 2017/0246033 A1 | 8/2017 | Bor et al. |
| 2017/0340483 A1 | 11/2017 | Rill et al. |
| 2017/0360604 A1 | 12/2017 | Bach et al. |
| 2018/0085257 A1 | 3/2018 | Horvath et al. |
| 2018/0104477 A1 | 4/2018 | Kurtz et al. |
| 2018/0125708 A1 | 5/2018 | Bohme et al. |
| 2018/0168737 A1 | 6/2018 | Ren et al. |
| 2018/0207029 A1 | 7/2018 | Herekar et al. |
| 2018/0214305 A1 | 8/2018 | Schuele et al. |
| 2018/0221199 A1 | 8/2018 | Heacock |
| 2018/0235462 A1 | 8/2018 | Gooi et al. |
| 2018/0344527 A1 | 12/2018 | Palanker et al. |
| 2019/0078073 A1 | 3/2019 | Streeter et al. |
| 2019/0099291 A1 | 4/2019 | Herekar et al. |
| 2019/0105200 A1 | 4/2019 | Hipsley |
| 2019/0105519 A1 | 4/2019 | Herekar et al. |
| 2019/0117459 A1 | 4/2019 | Berlin |
| 2019/0142636 A1 | 5/2019 | Tedford et al. |
| 2019/0151146 A1 | 5/2019 | Kim |
| 2019/0247225 A1 | 8/2019 | Stobrawa et al. |
| 2019/0269554 A1 | 9/2019 | Goldshleger et al. |
| 2019/0343680 A1 | 11/2019 | Belkin et al. |
| 2019/0344076 A1 | 11/2019 | Irazoqui et al. |
| 2019/0358085 A1 | 11/2019 | Fu et al. |
| 2020/0038245 A1 | 2/2020 | Hart et al. |
| 2020/0078216 A1 | 3/2020 | Raksi |
| 2020/0093639 A1 | 3/2020 | McCall, Jr. |
| 2020/0107724 A1 | 4/2020 | Wiltberger et al. |
| 2020/0146887 A1 | 5/2020 | Horvath et al. |
| 2020/0306080 A1 | 10/2020 | Herekar et al. |
| 2020/0345546 A1 | 11/2020 | Belkin et al. |
| 2020/0352785 A1 | 11/2020 | Holland et al. |
| 2020/0360187 A1 | 11/2020 | Schuele et al. |
| 2020/0379216 A1 | 12/2020 | Curatu et al. |
| 2021/0113373 A1 | 4/2021 | Sacks et al. |
| 2021/0267800 A1 | 9/2021 | Sacks et al. |
| 2021/0338484 A1 | 11/2021 | Hipsley |
| 2022/0031503 A1* | 2/2022 | Dorin ................ A61F 9/008 |
| 2022/0249861 A1 | 8/2022 | Belkin et al. |
| 2023/0201037 A1 | 6/2023 | Barrett et al. |
| 2023/0226372 A1 | 7/2023 | Herekar et al. |

FOREIGN PATENT DOCUMENTS

| | | |
|---|---|---|
| CA | 2640203 A1 | 8/2007 |
| CN | 1579351 A | 2/2005 |
| CN | 101411607 A | 4/2009 |
| CN | 201537172 U | 8/2010 |
| CN | 102193182 A | 9/2011 |
| CN | 105138996 A | 12/2015 |
| CN | 205698218 U | 11/2016 |
| CN | 108024870 A | 5/2018 |
| DE | 202016006265 U1 | 3/2017 |
| EP | 0224322 A1 | 6/1987 |
| EP | 0651982 A1 | 5/1995 |
| EP | 0689811 A1 | 1/1996 |
| EP | 1602321 A1 | 12/2005 |
| EP | 2301421 A1 | 3/2011 |
| EP | 2301424 B1 | 3/2011 |
| EP | 2301425 B1 | 3/2011 |
| EP | 2602005 A1 | 6/2013 |
| EP | 1856774 B1 | 6/2016 |
| EP | 2695016 B1 | 3/2017 |
| EP | 2992931 B1 | 8/2017 |
| EP | 2391318 B1 | 12/2017 |
| EP | 3329839 A1 | 6/2018 |
| EP | 2729099 B1 | 11/2019 |
| EP | 3191040 B1 | 7/2020 |
| EP | 3517081 B1 | 11/2020 |
| EP | 2854729 B1 | 3/2021 |
| FR | 2655837 A1 | 6/1991 |
| JP | 2007151739 A | 6/2007 |
| JP | 2010148635 A | 7/2010 |
| JP | 2016013255 A | 1/2016 |
| JP | 2018051210 A | 4/2018 |
| KR | 20180106113 A | 10/2018 |
| KR | 20190022216 A | 3/2019 |
| RU | 2499582 C1 | 11/2013 |
| RU | 2553507 C1 | 6/2015 |
| WO | 9216259 A1 | 10/1992 |
| WO | 1993012727 A1 | 7/1993 |
| WO | 9316631 A1 | 9/1993 |
| WO | 9412092 A1 | 6/1994 |
| WO | 9416425 A1 | 7/1994 |
| WO | 9515134 A1 | 6/1995 |
| WO | 1998022016 A2 | 5/1998 |
| WO | 9918868 A1 | 4/1999 |
| WO | 0195842 A1 | 12/2001 |
| WO | 02064031 A2 | 8/2002 |
| WO | 02087442 A1 | 11/2002 |
| WO | 2014018104 A1 | 1/2004 |
| WO | 2004027487 A1 | 4/2004 |
| WO | 2006119349 A2 | 11/2006 |
| WO | 2006119584 A1 | 11/2006 |

(56) References Cited

FOREIGN PATENT DOCUMENTS

| | | |
|---|---|---|
| WO | 2006128038 A2 | 11/2006 |
| WO | 2007103349 A2 | 9/2007 |
| WO | 2008112236 A1 | 9/2008 |
| WO | 2008118198 A2 | 10/2008 |
| WO | 2010094353 A1 | 8/2010 |
| WO | 2010113193 A1 | 10/2010 |
| WO | 2011017002 A2 | 2/2011 |
| WO | 2011163508 A2 | 6/2011 |
| WO | 2011085274 A1 | 7/2011 |
| WO | 2011151812 A1 | 12/2011 |
| WO | 2013004255 A1 | 1/2013 |
| WO | 2013035091 A1 | 3/2013 |
| WO | 2013059481 A1 | 4/2013 |
| WO | 2013059564 A1 | 4/2013 |
| WO | 2013122711 A1 | 8/2013 |
| WO | 2013165689 A1 | 11/2013 |
| WO | 2014025862 A1 | 2/2014 |
| WO | 2014132162 A1 | 9/2014 |
| WO | 2014191031 A1 | 12/2014 |
| WO | 2015069197 A1 | 5/2015 |
| WO | 2015119888 A1 | 8/2015 |
| WO | 2015130821 A2 | 9/2015 |
| WO | 2015131135 A1 | 9/2015 |
| WO | 2016018864 A1 | 2/2016 |
| WO | 2016058931 A2 | 4/2016 |
| WO | 2016156760 A1 | 10/2016 |
| WO | 2016187436 A1 | 11/2016 |
| WO | 2016207739 A1 | 12/2016 |
| WO | 2017023296 A1 | 2/2017 |
| WO | 2017031570 A1 | 3/2017 |
| WO | 2017069819 A1 | 4/2017 |
| WO | 2018005796 A1 | 1/2018 |
| WO | 2018021780 A1 | 2/2018 |
| WO | 2018049246 A1 | 3/2018 |
| WO | 2018152020 A1 | 8/2018 |
| WO | 2018232397 A1 | 12/2018 |
| WO | 2019109125 A1 | 6/2019 |
| WO | 2020008323 A1 | 1/2020 |
| WO | 2020012841 A1 | 1/2020 |
| WO | 2020018242 A1 | 1/2020 |
| WO | 2020018436 A1 | 1/2020 |
| WO | 2020050308 A1 | 3/2020 |
| WO | 202093060 A2 | 5/2020 |
| WO | 2020089737 A1 | 5/2020 |
| WO | 2020093060 A2 | 5/2020 |
| WO | 2020183342 A1 | 9/2020 |
| WO | 2021026538 A1 | 2/2021 |
| WO | 2021048723 A1 | 3/2021 |
| WO | 2021155445 A1 | 8/2021 |
| WO | 2021170664 A1 | 9/2021 |
| WO | 2022223690 A1 | 10/2022 |

OTHER PUBLICATIONS

JP Application # 2020561860 Office Action dated Feb. 7, 2023.
Kohnen et al., "Internal Anterior Chamber Diameter using Optical Coherence Tomography Compared with White-To-White Distances using Automated Measurements," Journal of Cataract & Refractive Surgery, vol. 32, pp. 1809-1813, Nov. 2006.
Zhang et al., "Perioperative Medications for Preventing Temporarily Increased Intraocular Pressure after Laser Trabeculoplasty (Review)," Cochrane Database of Systematic Reviews 2017, issue 2, pp. 1-117, year 2017.
Katta et al., "Optical Coherence Tomography Image-Guided Smart Laser Knife for Surgery," Lasers in Surgery and Medicine, Wiley Online Library, pp. 1-11, Jul. 2017.
Barnes et al., "Control of Intraocular Pressure Elevations after Argon Laser Trabeculoplasty: Comparison of Brimonidine 0.2% to Apraclonidine 1.0%," Opthalmology, vol. 106, No. 10, pp. 2033-2037, year 1999.
Yakopson et al., "Brimonidine 0.1% vs. Apraclonidine 0.5% for Prevention of Intraocular Pressure Elevation after Selective Laser Trabeculoplasty," Investigative Ophthalmology & Visual Science, vol. 49, p. 1234, May 2008.
Kim et at., "Effect of Prophylactic Topical Brimonidine (0.15%) Administration on the Development of Subconjunctival Hemorrhage after Intravitreal Injection," Retina, The Journal for Retinal and Vitreous Diseases, vol. 31, No. 2, pp. 389-392, year 2011.
Hong et al., "Effect of Prophylactic Brimonidine Instillation on Bleeding during Strabismus Surgery in Adults," American Journal of Ophthalmology, vol. 144, No. 3, pp. 469-470, Sep. 2007.
Goldsmith et al., "Anterior Chamber Width Measurement by High-Speed Optical Coherence Tomography," Ophthalmology, vol. 112, No. 2, pp. 238-244, year 2005.
Norden, "Effect of Prophilactic Brimonidine on Bleeding Complications and Flap Adherence After Laser in situ Keratomileusis," Journal of Refractive Surgery, vol. 18, No. 4, pp. 468-471, Jul./Aug. 2002.
Gophotonics, "NL200 series," Data Sheet, pp. 1-3, Jun. 29, 2017.
EP Application # 20201567.3 Office Action dated Jun. 6, 2023.
JP Application # 2020561860 Office Action dated Jun. 13, 2023.
JP Application # 2021516473 Office Action dated Jun. 20, 2023.
CN Application # 2020800563096 Office Action dated Jul. 1, 2023.
EP Application # 20864109.2 Search Report dated Aug. 10, 2023.
Gazzard et al., "Selective Laser Trabeculoplasty versus Drops for Newly Diagnosed Ocular Hypertension and Glaucoma: The LIGHT RCT," Health Technology Assessment, NHS, vol. 23, issue 31, pp. 1-132, Jun. 2019.
Kelley et al., "Stem Cells in the Trabecular Meshwork: Present and Future Promises," Experimental Eye Research, vol. 88, issue 4, pp. 747-751, Apr. 2009.
Dueker et al., "Stimulation of Cell Division by Argon and Nd:YAG Laser Trabeculoplasty in Cynomolgus Monkeys," Investigative Ophthalmology & Visual Science, vol. 31, No. 1, pp. 115-124, year 1990.
Nowell et al., "Corneal Epithelial Stem Cells and their Niche at a Glance," Cell Science at a Glance, vol. 130, Issue 6, pp. 1021-1025, year 2017.
Kim et al., "Diagnosis of Corneal Limbal Stem Cell Deficiency," Current Opinion in Ophthalmology, Wolters Kluwer Health, Inc., vol. 28, No. 4, pp. 355-362, Jul. 2017.
Gonzalez et al., "Limbal Stem Cells: Identity, Developmental Origin, and Therapeutic Potential," WIREs Developmental Biology, Wiley, vol. 7, issue 2, pp. 1-23, Mar. 2018.
Sepehr, "Corneal Endothelial Cell Dysfunction: Etiologies and Management," Therapeutic Advances in Opthalmology, pp. 1-19, year 2018.
Walshe et al., "Serial Explant Culture Provides Novel Insights into the Potential Location and Phenotype of Corneal Endothelial Progenitor Cells," Experimental Eye Research, vol. 127, pp. 9-13, year 2014.
Pinnamaneni et al., "Concise Review: Stem Cells in the Corneal Stroma," Stem Cells, vol. 30, issue 6, pp. 1059-1063, year 2012.
Espana et al., "Existence of Corneal Endothelial Slow-Cycling Cells," Investigative Ophthalmology & Visual Science, vol. 56, No. 6, pp. 3827-3837, Jun. 2015.
EP Application # 21885460.2 Search Report dated Aug. 26, 2024.
EP Application # 19830473.5 Office Action dated Sep. 3, 2024.
U.S. Appl. No. 17/273,323 Office Action dated Oct. 30, 2024.
U.S. Appl. No. 17/427,926 Office Action dated Aug. 27, 2024.
U.S. Appl. No. 17/427,926 Office Action dated May 9, 2024.
EP Application # 19877990.2 Office Oction dated May 13, 2024.
EP Application # 24158977.9 Search Report dated May 15, 2024.
EP Applicatian # 21845437.9 Search Report dated Jun. 19, 2024.
JP Application # 2023217477 Office Action dated Jul. 9, 2024.
U.S. Appl. No. 17/273,323 Office Action dated Jun. 18, 2024.
Nagar et al., "A randomised, prospective study comparing selective laser trabeculoplasty with latanoprost for the control of intraocular pressure in ocular hypertension and open angle glaucoma," British Journal of Ophthalmology, vol. 89, pp. 1413-1417, year 2005.
Hong et al., "Repeat Selective Laser Trabeculoplasty," Journal of Glaucoma, vol. 18, issue 3, pp. 180-183, Mar. 2009.
Goyal et al., "Effect of primary selective laser trabeculoplasty on tonographic outflow facility—a randomised clinical trial," British Journal of Ophthalmology, BMJ Publishing Group, vol. 94, issue 11, pp. 1-22, year 2010.

(56) References Cited

OTHER PUBLICATIONS

Franco et al., "Effect of Second SLT on IOP," Investigative Ophthalmology & Visual Science, vol. 48, pp. 1-2, May 2007.
Chen et al., "A Comparison between 90 degrees and 180 degrees Selective Laser Trabeculoplasty," Journal of Glaucoma, vol. 13, issue 1, p. 1, Feb. 2004.
Mequio et al., "Efficacy of Repeat Selective Laser Trabeculoplasty," Investigative Ophthalmology & Visual Science, vol. 48, p. 1, year 2007.
Grulkowski et al., "Anterior segment imaging with Spectral OCT system using a high-speed CMOS camera," Optics Express, vol. 17, No. 6, p. 4842-4858, year 2009.
Shields et al., "Noncontact Transscleral ND:YAG Cyclophotocoagulation: A Long-Term Follow-Up of 500 Patients," Transactions of the American Ophthalmological Society, vol. XCII, pp. 271-287, year 1994.
Liu et al., "Real-time visual analysis of microvascular blood flow for critical care," CVPR2015 paper as Open Access Version, provided by the Computer Vision Foundation, pp. 2217-2225, year 2015.
Desco et al., "Effect of prophylactic brimonidine on bleeding complications after cataract surgery," European Journal of Ophthalmology, vol. 15, pp. 228-232, year 2005.
Pasquali et al., "Dilute brimonidine to improve patient comfort and subconjunctival hemorrhage after LASIK," Journal of Refractive Surgery, vol. 29, pp. 469-475, year 2013.
Sacks et al., "Non-contact direct selective laser trabeculoplasty: light propagation analysis," Biomedical Optics Express, vol. 11, pp. 2889-2904, year 2020.
Kasuga et al., "Trabecular Meshwork Length in Men and Women by Histological Assessment," Current Eye Research, Early Online, pp. 1-5, Jun. 2012.
Navilas Operator Manual, Document Version 2.10, 2012 OD-OS GmbH, pp. 1-94, Sep. 2012.
SensoMotoric Instruments GmbH (SMI), "SG 3000", Product Flyer, pp. 1-2, year 2010.
Ashik et al., "The precision of ophthalmic biometry using calipers," Canadian Journal of Ophthalmology, vol. 48, Issue 6, pp. 1-13, Dec. 2013.
Balalzsi, "Noncontact Thermal Mode Nd:YAG Laser Transscleral Cyclocoagulation in the Treatment of Glaucoma," Ophthalmology, vol. 98, pp. 1858-1863, year 1991.
Leung et al., "Anterior chamber angle imaging with optical coherence tomography," Eye, vol. 25, pp. 261-267, year 2011.
Tasman et al., "The Wills Eye Hospital Atlas of Clinical Ophthalmology," Lippincott Williams & Wilkins, p. 158, year 2001.
Gaasterland, "Laser Therapies: Iridotomy, Iridoplasty, and Trabeculoplasty," as appears in "The Glaucoma Book: A Practical Evidence-Based Approach to Patient Care," Springer, p. 722, year 2010.
Kara, "Bleeding in Retinal Images Using Image Processing", A Thesis submitted to the graduate school of applied sciences of Near East University, Nicosia, Larnaca, pp. 1-79, year 2019.
CN Application # 201980070459X Office Action dated Dec. 23, 2022.
"Smart Selecta Duet—Your Smart Selection for Glaucoma Care," Product Brochure, pp. 1-6, The Lumenis Group of Companies, year 2018.
Rashad, "How to do YAG Laser Posterior Capsulotomy in Small Pupil?", YouTube Clip, p. 1, Jul. 19, 2020 https://www.youtube.com/watch?v=12c39BoNBjM.
Quantel Medical, "Optimis II", datasheet, pp. 1-4, Aug. 5, 2022.
Variscite, "DART-MX8M", Datasheet, pp. 1-92, Feb. 2021.
Rashad, "What is the Easiest Way to do YAG Laser Posterior Capsulotomy?", YouTube Clip, p. 1, Jul. 17, 2020 https://www.youtube.com/watch?v=g0pV3UGo_20.
International Application PCT/IB2021/054187 search report dated Jul. 30, 2021.
Vogel et al., "Optical properties of human sclera, and their consequences for transscleral laser applications.", Lasers In Surgery and Medicine , vol. 11, pp. 331-340,year 1991.
Geffen et al., "Transscleral Selective Laser Trabeculoplasty Without a Gonioscopy Lens", Journal of Glaucoma, Inc, vol. 26, No. 3, pp. 201-207, Mar. 2017.
Das et al., "Sclera Recognition—A Survey", 2nd IAPR Asian Conference on Pattern Recognition, pp. 1-5, year 2013.
Kaya et al., "Designing A Pattern Stabilization Method Using Scleral Blood Vessels For Laser Eye Surgery", International Conference on Pattern Recognition, pp. 698-701, Istanbul, Turkey, Aug. 23-26, year 2010.
Barkana et al., "Selective Laser Trabeculoplasty", Survey of Ophthalmology, vol. 52, No. 6, pp. 634-653, year 2007.
Arany, "Photobiomodulation therapy: Easy to do, but difficult to get right", LaserFocusWorld, pp. 1-6, Jul. 31, 2019 downloaded from www.laserfocusworld.com/lasers-sources/article/14037967/photobiomodulation-therapyeasy-to-do-put-difficult-to-get-right, pp. 22-24, year 2019.
Borzabadi-Farahani, "Effect of low-level laser irradiation on proliferation of human dental mesenchymal stem cells; a systemic review", Journal of Photochemistry and Photobiology B: Biology, vol. 162, pp. 577-582, Sep. 2016.
Acott et al., "Trabecular Repopulation by Anterior Trabecular Meshwork Cells After Laser Trabeculoplasty", American Journal of Ophthalmology, vol. 107, issue 1, pp. 1-6, Jan. 1989.
Cao et al., "Peripheral Iridotomy," Medscape 25, pp. 1-12, Jun. 15, 2020.
Husain, "Laser Peripheral Iridotomy—Practical Points", YouTube presentation, p. 1, Sep. 28, 2016, downloaded from https://www.youtube.com/watch ?=Azxzsv31yls.
Ivandic et al., "Early Diagnosis of Ocular Hypertension Using a Low-Intensity Laser Irradiation Test", Photomedicine and Laser Surgey, vol. 00, No. 00, pp. 1-5, year 2009.
Smith et al., "Light scatter from the central human cornea", Journal "Eye", issue 4, pp. 584-588, year 1990.
Turati et al., "Patterned Laser Trabeculoplasty", Ophthalmic Surgery, Lasers and Imaging , vol. 41, No. 5, pp. 538-545, 2010.
Nozaki et al., "Patterned Laser Trabeculoplasty with PASCAL streamline 577", Investigative Ophthalmology & Visual Science, vol. 54, p. 1867, Jun. 2013.
Acktar, "Magic Black Coatings", Product Information, pp. 1-6, year 2017.
Acktar, "Fractal Black Coating", Product Information, pp. 1-5, year 2017.
Cloudy Nights LLC, "Cloudy Nights—Equipment Discussions—ATM", Optics and DIY Forum, pp. 1-5, Feb. 15, 2015.
Defense Tech, "Anti-Laser Contact Lenses", Product Information, p. 1-1, Nov. 29, 2004.
IEC standard 60825-1, "Safety of Laser Products", Edition 1.2, pp. 1-122, years 2001-2008.
Laser Safety Industries, "Filter Specifications", pp. 1-5, year 2008.
Thorlabs, "Laser Safety Glasses", Product Information, p. 1, Nov. 3, 2014.
Surrey Nanosystems Ltd, "Vantablack", Data Sheet, pp. 1-4, Mar. 1, 2016.
International Application # PCT/IB2023/061472 Search Report dated Feb. 29, 2024.
Danielson et al., Fixed High-Energy versus Standard Titrated Energy Settings for Selective Laser Trabeculoplasty, Journal of Glaucoma Publish Ahead of Print, Wolters Kluwer Health, Inc., pp. 1-16, year 2023.
Radcliffe et al., "Energy Dose-Response in Selective Laser Trabeculoplasty: A Review," Journal of Glaucoma, vol. 31, pp. e49-e68, year 2022.
Gazzard, "A Brief Guide to Gonioscopy," Video Clip, Optometry today, pp. 1-2, May 21, 2015, as downloaded from https://www.youtube.com/watch?v=8yTTbHWxUik.
Alward et al., "Principles of Gonioscopy," Color Atlas of Gonioscopy, American Academy of Opthalmology, pp. 1-10, Nov. 8, 2017, as downloaded from https://www.aao.org/education/disease-review/principles-of-gonioscopy.

(56) References Cited

OTHER PUBLICATIONS

Nolan et al., "Gonioscopy skills and techniques," Community Eye Health Journal, vol. 34, No. 112, pp. 40-42, year 2021.
Breazzano et al., "Analysis of Schwalbe's Line (Limbal Smooth Zone) by Scanning Electron Microscopy and Optical Coherence Tomography in Human Eye Bank Eyes," Journal of Ophthalmic and Vision Research, vol. 8, issue 1, pp. 9-16, Jan. 2013.
Thorlabs, Inc., "CPS520—Collimated Laser Diode Module, 520 nm, 4.5 mW, Elliptical Beam, Ø11 mm," Product Details, pp. 1-1, years 1999-2023, as downloaded from https://www.thorlabs.com/thorproduct.cfm?partnumber=CPS520.
Prophotonix, "Green Laser Modules," Product Information, pp. 1-8, year 2024, as downloaded from https://www.prophotonix.com/led-and-laser-products/laser-modules/laser-modules-color/green-laser-modules/.
Idex Helath & Science Llc, "532 nm StopLine® single-notch filter," Product Details, pp. 1-2, year 2023 as downloaded from https://www.idex-hs.com/store/product-detail/nf03_532e_25/fl-009362?cat_id=products&node=individual_optical_filters.
Brackley et al., "Lecture: Using the Slit Lamp Microscope to Visualize the Ocular Structures," Video Clip, pp. 1-2, Sep. 17, 2022, as downloaded from https://www.youtube.com/watch?v=1E-sEhy9tBo.
Bruce et al., "Zoom in on Gonioscopy," Review of Optometry, pp. 1-8, Sep. 1, 2016, as downloaded from https://www.reviewofoptometry.com/article/zoom-in-on-gonioscopy.
AU Application # 2022211843 Office Action dated Jan. 8, 2024.
JP Application # 2022508451 Office Action dated Mar. 5, 2024.
AU Application # 2021369792 Office Action dated Mar. 21, 2024.
Root, "How to perform a Laser Iridotomy (Video)," pp. 1-14, year 2010, as downloaded from https://timroot.com/how-to-perform-a-laser-iridotomy-video/.
AU Application # 2022211843 Office Action dated Sep. 27, 2023.
AU Application # 2021311097 Office Action dated Sep. 28, 2023.
U.S. Appl. No. 17/427,926 Office Action dated Oct. 17, 2023.
JP Application # 2021536316 Office Action dated Oct. 24, 2023.
JP Application # 2020561860 Office Action dated Oct. 31, 2023.
JP Application # 2021516473 Office Action dated Nov. 7, 2023.
SG Application # 11202010437T Office Action Dec. 5, 2023.
U.S. Appl. No. 17/735,153 Office Action dated Dec. 18, 2023.
U.S. Appl. No. 17/136,052 Office Action dated Dec. 22, 2023.
U.S. Appl. No. 17/427,926 Office Action dated Dec. 22, 2023.
International Application # PCT/IB2023/060104 Search Report Dec. 26, 2023.
Sridhar, "Anatomy of Cornea and Ocular Surface," Indidan Journal of Ophthalmology, vol. 66, issue 2, pp. 190-194, year 2018.
JP Application # 2022567443 Office Action dated Dec. 17, 2024.
U.S. Appl. No. 17/627,701 office action dated Jul. 2, 2025.
CN Application # 2021800715816 office action dated Apr. 25, 2025.
JP Application # 2022-567443 office action dated May 15, 2025.

\* cited by examiner

AUTOMATED CAPSULOTOMY

CROSS-REFERENCE TO RELATED APPLICATIONS

The present application claims the benefit of U.S. Provisional Application 63/053,650, entitled "Automatic posterior capsulotomy and combination device," filed Jul. 19, 2020, whose disclosure is incorporated herein by reference.

FIELD OF THE INVENTION

The present invention is related to ophthalmologic procedures, especially capsulotomy procedures.

BACKGROUND

In some cases, following the replacement of the natural lens of an eye, opacification of the posterior capsule of the eye occurs. In such cases, a posterior capsulotomy may be the treatment of choice.

U.S. Pat. No. 8,465,478 describes systems, apparatus, and methods for developing laser systems that can create a precise predetermined jigsaw capsulotomy. The systems, apparatus, and methods further provide laser systems that can use a single laser as a therapeutic laser and as laser radar and that reduce the patient-to-patient variability and doctor-to-doctor variability associated with hand-held apparatus for performing capsulorhexis and capsulotomies. There is further described a precise predetermined jigsaw shot pattern and shaped capsulotomy that is based at least in part on the shape of an IOL and in particular an accommodating IOL.

U.S. Pat. No. 8,845,625 describes systems and methods for cataract intervention. In one embodiment a system comprises a laser source configured to produce a treatment beam comprising a plurality of laser pulses; an integrated optical system comprising an imaging assembly operatively coupled to a treatment laser delivery assembly such that they share at least one common optical element, the integrated optical system being configured to acquire image information pertinent to one or more targeted tissue structures and direct the treatment beam in a 3-dimensional pattern to cause breakdown in at least one of the targeted tissue structures; and a controller operatively coupled to the laser source and integrated optical system, and configured to adjust the laser beam and treatment pattern based upon the image information, and distinguish two or more anatomical structures of the eye based at least in part upon a robust least squares fit analysis of the image information.

U.S. Pat. No. 10,143,590 describes a method and apparatus for performing a laser-assisted posterior capsulotomy and for performing laser eye surgery on an eye having a penetrated cornea. A method for performing a posterior capsulotomy includes injecting fluid between the lens posterior capsule and the anterior hyaloids membrane to separate the lens posterior capsule and the anterior hyaloids membrane. With the lens posterior capsule separated from the anterior hyaloids membrane, a posterior capsulotomy is performed on the lens posterior capsule by using a laser to incise the lens posterior capsule.

U.S. Pat. No. 10,849,789 describes an ophthalmic measurement and laser surgery system, including: a laser source; a corneal topography subsystem; an axis determining subsystem; a ranging subsystem comprising an Optical Coherence Tomographer (OCT); and a refractive index determining subsystem. All of the subsystems are under the operative control of a controller. The controller is configure to: operate the corneal topography subsystem to obtain corneal surface information; operate the axis determining subsystem to identify one or more ophthalmic axes of the eye; operate the OCT to sequentially scan the eye in a plurality of OCT scan patterns, the plurality of scan patterns configured to determine an axial length of the eye; operate the refractive index determining subsystem so to determine an index of refraction of one or more ophthalmic tissues, wherein at least one of the corneal surface information, ophthalmic axis information, and axial length is modified based on the determined index of refraction.

SUMMARY OF THE INVENTION

There is provided, in accordance with some embodiments of the present invention, a system, including a radiation source and a controller. The controller is configured to define a treatment zone on a capsule of an eye of a subject, and to form an opening in the capsule, subsequently to defining the treatment zone, by irradiating multiple target regions within the treatment zone in an iterative process. The iterative process includes, during each one of multiple iterations of the process, acquiring an image of at least part of the capsule, based on the acquired image, designating one of the target regions, and causing the radiation source to irradiate the designated target region.

In some embodiments, the capsule is a posterior capsule.

In some embodiments, the controller is configured to define the treatment zone by:

based on at least one initial image of the eye, identifying an anterior-capsule opening in an anterior capsule of the eye, and defining the treatment zone such that the treatment zone lies entirely behind the anterior-capsule opening.

In some embodiments, the controller is configured to define the treatment zone by:

based on at least one initial image of the eye, identifying an edge of an iris of the eye, and defining the treatment zone such that the treatment zone lies entirely within the edge.

In some embodiments, the controller is configured to define the treatment zone by:

based on at least one initial image of the eye, identifying one or more features of a prosthetic intraocular lens (IOL) in the eye, in response to the features, calculating an estimated position of the IOL, and defining the treatment zone in response to the estimated position.

In some embodiments, during at least one of the iterations, designating the target region includes:

based on the acquired image, identifying tissue of the capsule at a last-designated one of the target regions, and in response to identifying the tissue, redesignating the last-designated one of the target regions.

In some embodiments, during at least one of the iterations, designating the target region includes:

based on the acquired image, identifying a portion of a perimeter of the opening that is farther from a boundary of the treatment zone than are other portions of the perimeter, and designating the target region at a predefined distance from the identified portion of the perimeter.

In some embodiments, during at least one of the iterations, designating the target region includes:

based on the image, identifying a fold within the treatment zone, and in response to identifying the fold, designating the target region such that the target region overlaps the fold.

In some embodiments, during at least one of the iterations, designating the target region includes:

based on the acquired image, ascertaining that a perimeter of the opening is stable, and in response to the ascertaining, designating the target region.

In some embodiments, the controller is configured to form the opening subsequently to a designation of a sequence of tentative target regions, and during at least one of the iterations, designating the target region includes:

based on the acquired image, ascertaining that a distance between a next one of the tentative target regions and a perimeter of the opening is greater than a predefined threshold distance, and in response to ascertaining that the distance is greater than the predefined threshold distance, designating, as the target region, the next one of the tentative target regions.

In some embodiments, during at least one other one of the iterations, designating the target region includes:

based on the acquired image, ascertaining that the distance is not greater than the predefined threshold distance, and in response to ascertaining that the distance is not greater than the predefined threshold distance, designating, as the target region, the tentative target region following the next one of the tentative target regions.

In some embodiments, during at least one other one of the iterations, designating the target region includes:

based on the acquired image, ascertaining that the distance is not greater than the predefined threshold distance, and in response to ascertaining that the distance is not greater than the predefined threshold distance, designating the target region by applying an offset to a location of the next one of the tentative target regions.

In some embodiments, the controller is further configured to:

define a target boundary on the capsule, and terminate the iterative process in response to ascertaining that the opening reaches a predefined threshold percentage of the target boundary.

In some embodiments, the controller is configured to define the target boundary by placing the target boundary at a predefined offset inward from a boundary of the treatment zone.

There is further provided, in accordance with some embodiments of the present invention, a method, including defining a treatment zone on a capsule of an eye of a subject and, subsequently to defining the treatment zone, forming an opening in the capsule by irradiating multiple target regions within the treatment zone in an iterative process. The iterative process includes, during each one of multiple iterations of the process, acquiring an image of at least part of the capsule, based on the acquired image, designating one of the target regions, and causing a radiation source to irradiate the designated target region.

There is further provided, in accordance with some embodiments of the present invention, a computer software product including a tangible non-transitory computer-readable medium in which program instructions are stored. The instructions, when read by a controller, cause the controller to define a treatment zone on a capsule of an eye of a subject, and to form an opening in the capsule, subsequently to defining the treatment zone, by irradiating multiple target regions within the treatment zone in an iterative process. The iterative process includes, during each one of multiple iterations of the process, acquiring an image of at least part of the capsule, based on the acquired image, designating one of the target regions, and causing the radiation source to irradiate the designated target region.

The present invention will be more fully understood from the following detailed description of embodiments thereof, taken together with the drawings, in which:

DETAILED DESCRIPTION OF EMBODIMENTS

Overview

Conventional capsulotomy procedures require a specialist physician who has undergone extensive training. Unfortunately, however, such physicians may be in short supply.

To address this challenge, embodiments of the present invention provide an automated capsulotomy system, which allows even a physician who has undergone a lesser amount of training to perform the procedure. The system comprises a radiation source, a camera, a controller, and suitable optics. Based on images acquired by the camera, the controller controls the radiation source and optics so as to form an opening in the posterior capsule by irradiating the capsule.

Typically, the controller first defines a treatment zone, which includes at least some of the opacified portion of the posterior capsule. Next, the controller designates a first target region, typically at the center of the treatment zone, and then irradiates the first target region. After confirming, from an image of the capsule, that an opening was initialized at the first target region, the controller designates a second target region at a suitable distance from the perimeter of the opening, and then irradiates the second target region. After confirming, from another image of the capsule, that the opening was expanded, the controller designates and then irradiates a third target region. In this manner, the controller uses image processing to optimize the designation of the target regions, thus facilitating expanding the opening more efficiently, i.e., using fewer radiation beams. Upon ascertaining, from another image, that the opening has been sufficiently enlarged, the controller terminates the procedure.

Typically, the controller is configured to identify, by image processing, any folds in the posterior capsule. In response to identifying a fold, a target region overlapping the fold may be designated. Advantageously, by targeting folds in the capsule, the opening may be expanded more efficiently.

In some embodiments, a sequence of tentative target regions is designated prior to any irradiation of the capsule. Subsequently, the controller iterates through the tentative target regions. For each tentative target region, based on the proximity of the tentative target region to the perimeter of the opening, the controller decides whether to irradiate the tentative target region, skip the tentative target region, or irradiate a new target region that is offset from the tentative target region.

In addition to performing an automated capsulotomy of a posterior capsule as described herein, the controller may form slit-shaped openings in the anterior capsule of the eye. Alternatively or additionally, the controller may use any of the techniques described herein to form a larger opening in the anterior capsule.

System Description

Figure 1:
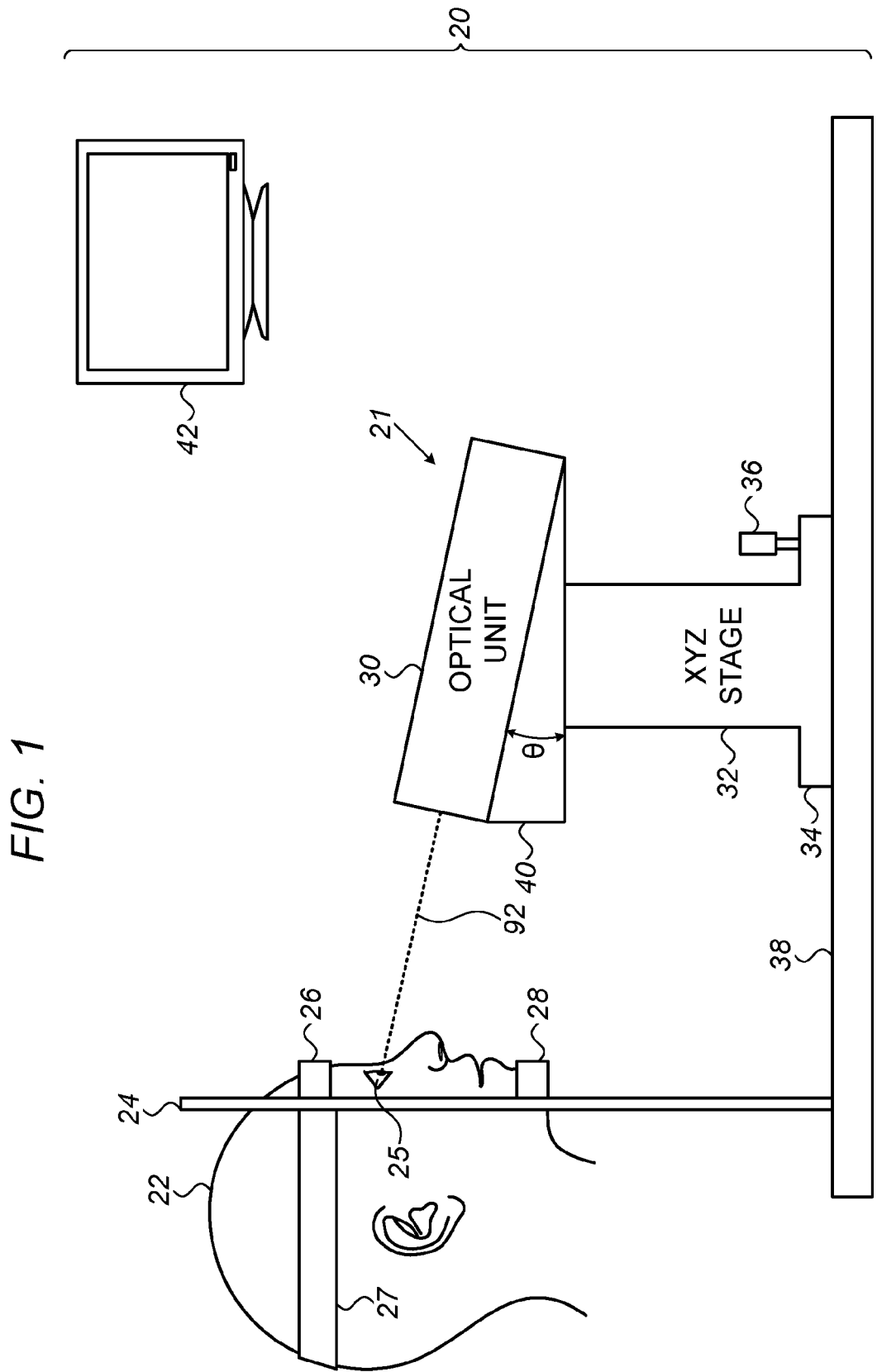
FIG. 1 is a schematic illustration of a system for performing a capsulotomy on a capsule of an eye of a patient, in accordance with some embodiments of the present invention.
Figure 2:
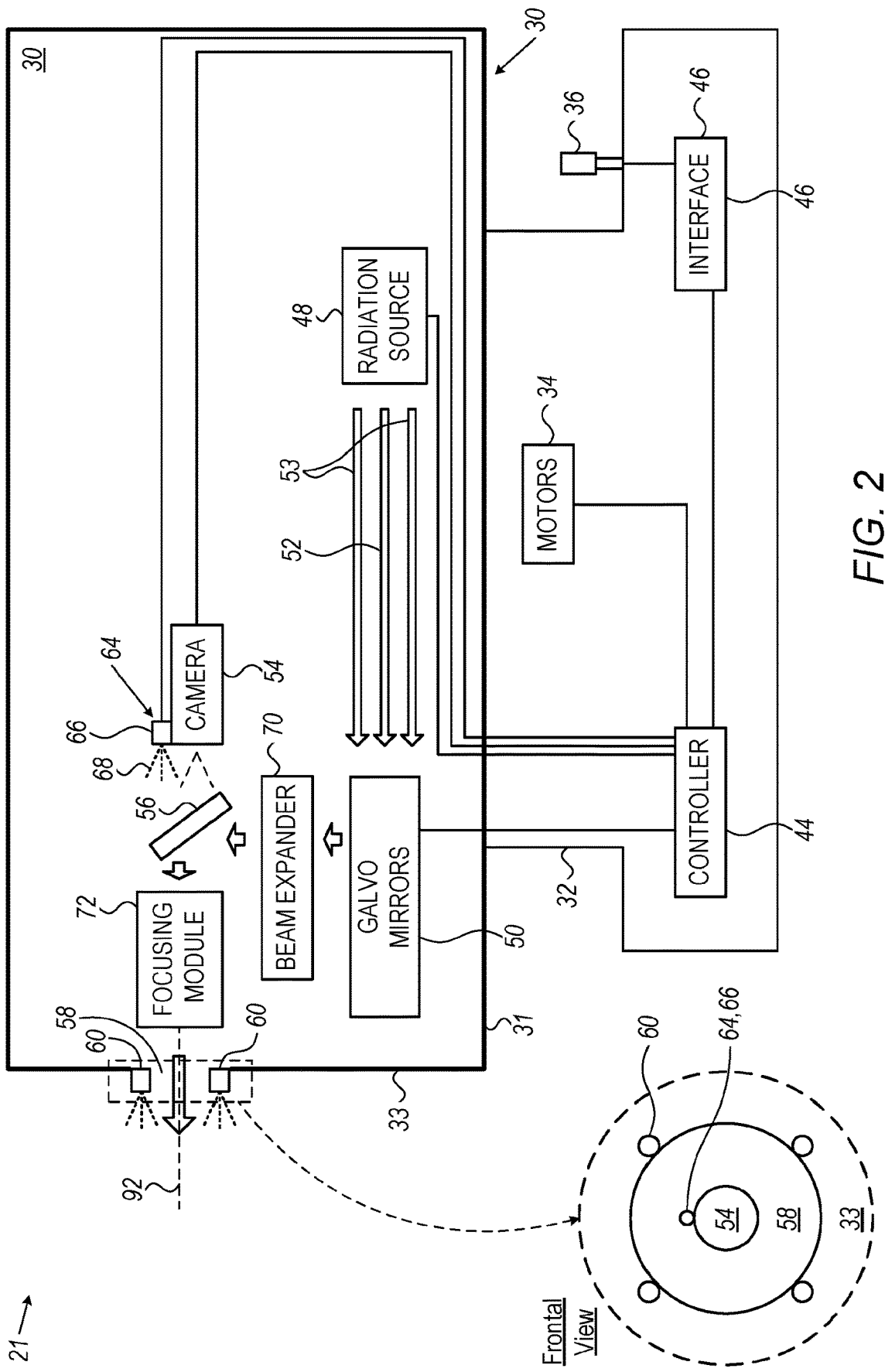
FIG. 2 is a schematic illustration of a capsulotomy device, in accordance with some embodiments of the present invention.

Reference is initially made to FIG. 1, which is a schematic illustration of a system 20, comprising a capsulotomy device 21, for performing a capsulotomy on a capsule of an eye 25 of a patient 22, in accordance with some embodiments of the present invention. Reference is further made to FIG. 2, which is a schematic illustration of capsulotomy device 21, in accordance with some embodiments of the present invention.

Capsulotomy device 21 comprises an optical unit 30 and a controller 44. Optical unit 30 comprises one or more beam-directing elements, comprising, for example, one or more galvo mirrors 50, which may be referred to collectively as a "galvo scanner," and/or a beam combiner 56. Optical unit 30 further comprises a radiation source 48, which is configured to irradiate the capsule of eye 25 with one or more treatment beams 52 by emitting the treatment beams toward the beam-directing elements such that the beams are directed by the beam-directing elements toward the capsule. Typically, radiation source 48 is further configured to irradiate the capsule with a pair of aiming beams 53, which are configured to overlap one another only when the distance of the optical unit from the capsule and the positioning of the beam-directing elements provide a desired treatment spot size on the capsule. Thus, aiming beams 53 may be used to verify the spot size of each treatment beam prior to emitting the treatment beam, as further described below with reference to FIG. 8.

In some embodiments, optical unit 30 further comprises one or more other optics. For example, the optical unit may comprise a beam expander 70, which expands and then re-collimates treatment beams 52. In such embodiments, typically, optical unit 30 further comprises a focusing module (comprising, for example, an F-theta lens or another type of lens), configured to focus the treatment beams.

More specifically, before the emission of each treatment beam 52 from radiation source 48, or while the beam is being emitted, controller 44 aims the beam-directing elements at a target region of the capsule such that the beam is directed, by the beam-directing elements, toward the target region. For example, the beam may be deflected by galvo mirrors 50 through beam expander 70 toward beam combiner 56, and then deflected by the beam combiner through focusing module 72, such that the beam impinges on the target region with the desired spot size. (Since each treatment beam impinges on the capsule with a non-infinitesimal spot size, the present application generally describes each beam as impinging on a "region" of the capsule, rather than impinging at a "point.") The beam thus follows a path 92, which extends from the most downstream of the beam-directing elements—such as focusing module 72—to the target region.

Typically, the radiation source comprises a laser, such as an Nd:YAG laser. (Examples of off-the-shelf products incorporating an Nd:YAG laser include Optimis II by Quantel Medical of Cournon-d'Auvergne, France, and Selecta Duet by Lumenis of Yokneam, Israel.) The laser may be modified to include an attenuator, an energy meter, and/or a mechanical shutter. Alternatively or additionally to a laser, the radiation source may comprise any other suitable emitter of radiation.

In some embodiments, the treatment beams include visible light. Alternatively or additionally, the treatment beams may include non-visible electromagnetic radiation, such as microwave radiation, infrared radiation, X-ray radiation, or gamma radiation. Typically, the wavelength of the treatment beams is between 400 and 1400 nm, e.g., 532 nm or 1064 nm.

Typically, the spatial profile of each treatment beam 52 on the capsule is approximately circular, e.g., with a spot size less than 22 μm. Alternatively, the spatial profile of each treatment beam 52 may be elliptical, square, or of any other suitable shape. In general, the size and shape of the treatment beam spots are chosen so as to deliver sufficient energy for photodisruption of the capsule.

Typically, the aiming beams include visible light, e.g., with a wavelength of between 600 and 700 nm.

Optical unit 30 further comprises a camera 54, which is used by controller 44 to acquire images of the eye. As shown in FIG. 2, camera 54 is typically aligned, at least approximately, with path 92; for example, the angle between path 92 and a hypothetical line extending from eye 25 to the camera may be less than 15 degrees. In some embodiments, the camera is positioned behind beam combiner 56, such that the camera receives light via the beam combiner. In other embodiments, the camera is offset from the beam combiner.

At the start of the procedure, camera 54 acquires an initial image of the capsule, or at least a portion thereof. Based on the image, controller 44 defines a treatment zone on the capsule, as further described below with reference to FIG. 3. Subsequently, during the procedure, camera 54 acquires multiple images of the capsule, or at least a portion thereof, at a relatively high frequency. Controller 44 processes these images and, in response thereto, designates target regions within the treatment zone for irradiation, as further described below with reference to the subsequent figures.

In general, camera 54 may comprise one or more imaging sensors of any suitable type(s), such as a charge-coupled device (CCD) sensor, a complementary metal-oxide-semiconductor (CMOS) sensor, an optical coherence tomography (OCT) sensor, and/or a hyperspectral image sensor. Using the sensors, the camera may acquire two-dimensional or three-dimensional images of any suitable type, such as monochrome images, color images (based, for example, on three color frames), multispectral images, hyperspectral images, optical coherence tomography (OCT) images, or images produced by fusing multiple images of different respective types.

Typically, optical unit 30 further comprises a light source 66, which is aligned, at least approximately, with path 92. For example, the angle between path 92 and a hypothetical line extending from the end of path 92 on eye 25 to light source 66 may be less than 20 degrees, such as less than 10 degrees. Light source 66 is configured to function as a fixation target 64 by transmitting visible fixation light 68, thus helping to stabilize the position of the eye. In particular, prior to the procedure, patient 22 is instructed to fixate eye 25 on light source 66. Subsequently, during the procedure, by virtue of light source 66 transmitting fixation light 68, eye 25 fixates on the light source, such that the eye's line-of-sight is approximately coincident with path 92 (due to the light source being approximately aligned with the path) and the eye is relatively stable. While the eye fixates on the light source, the radiation source irradiates the capsule of the eye with treatment beams 52.

In some embodiments, light source 66 comprises a light emitter, such as a light emitting diode (LED). In other embodiments, the light source comprises a reflector configured to reflect light emitted from a light emitter.

Typically, the wavelength of fixation light 68, which may be higher or lower than that of the treatment beams, is between 350 and 850 nm. For example, fixation light 68 may be orange or red, with a wavelength of 600-750 nm.

Typically, the optical unit comprises an optical bench, and at least some of the aforementioned components belonging to the optical unit, such as the radiation source, the galvo mirrors, and the beam combiner, are coupled to the optical bench. Typically, the optical unit further comprises a front face 33, through which the treatment beams and the fixation light pass. For example, optical unit 30 may comprise an encasement 31, which at least partially encases the optical bench and comprises front face 33. (Encasement 31 may be made of a plastic, a metal, and/or any other suitable material.) Alternatively, front face 33 may be attached to, or may be an integral part of, the optical bench.

In some embodiments, front face 33 is shaped to define an opening 58, through which the treatment beams and fixation light pass. In other embodiments, the front face comprises an exit window in lieu of opening 58, such that fixation light 68 and treatment beams 52 pass through the exit window. The exit window may be made of a plastic, a glass, or any other suitable material that is generally transparent to the treatment beams, aiming beams, fixation light 68, and any light used for imaging the eye, such as light from the illumination sources 60 described below.

Optical unit 30 is mounted onto an XYZ stage unit 32, which is controlled by a control mechanism 36, such as a joystick. Using control mechanism 36, the user of system 20 may position the optical unit (e.g., by adjusting the distance of the optical unit from the eye) prior to treating the eye. In some embodiments, XYZ stage unit 32 comprises locking elements configured to inhibit motion of the stage unit following the positioning of the stage unit.

In some embodiments, XYZ stage unit 32 comprises one or more motors 34, and control mechanism 36 is connected to interface circuitry 46. As the user manipulates the control mechanism, interface circuitry 46 translates this activity into appropriate electronic signals, and outputs these signals to controller 44. In response to the signals, the controller controls motors 34.

In other embodiments, XYZ stage unit 32 is controlled manually by manipulating the control mechanism. In such embodiments, the XYZ stage unit may comprise a set of gears instead of motors 34.

System 20 further comprises a headrest 24, comprising a forehead rest 26 and a chinrest 28. During the capsulotomy, patient 22 presses his forehead against forehead rest 26 while resting his chin on chinrest 28. In some embodiments, headrest 24 further comprises an immobilization strap 27, configured to secure the patient's head from behind and thus keep the patient's head pressed against the headrest.

In some embodiments, system 20 further comprises a contact lens, configured to focus the treatment beams and/or stabilize eye 25 while contacting the eye.

In some embodiments, as shown in FIG. 1, headrest 24 and XYZ stage unit 32 are both mounted onto a surface 38, such as the top surface of a tray or table. In other embodiments, the XYZ stage unit is mounted onto surface 38, and the headrest is attached to the XYZ stage unit.

System 20 further comprises a monitor 42, configured to display the images of the eye acquired by the camera. Monitor 42 may be attached to optical unit 30 or disposed at any other suitable location, such as on surface 38 next to device 21. In some embodiments, monitor 42 comprises a touch screen, such that the user may input commands and/or information to the system via the touch screen. Alternatively or additionally, system 20 may comprise any other suitable input devices, such as a keyboard or a mouse, which may be used by the user.

In some embodiments, monitor 42 is connected directly to controller 44 over a wired or wireless communication interface. In other embodiments, monitor 42 is connected to controller 44 via an external processor, such as a processor belonging to a standard desktop computer.

In some embodiments, as shown in FIG. 2, controller 44 is disposed within XYZ stage unit 32. In other embodiments, controller 44 is disposed externally to the XYZ stage unit. Alternatively or additionally, the controller may cooperatively perform at least some of the functionality described herein with another, external processor.

In some embodiments, system 20 is also configured to perform trabeculoplasty procedures, e.g., as described in International Patent Application Publication WO/2020/008323, whose disclosure is incorporated herein by reference. Thus, using system 20, a trabeculoplasty procedure may be performed on patient 22 before or after a capsulotomy procedure is performed on the patient; for example, both procedures may be performed during a single sitting of patient 22.

In such embodiments, the treatment wavelength used for trabeculoplasty procedures (e.g., 532 nm) may be the same as that used for capsulotomy procedures. Alternatively, radiation source 48 may comprise a wavelength converter, configured to convert the wavelength of the treatment beams from a first wavelength used for capsulotomy procedures (e.g., 1064 nm) to a second wavelength used for trabeculoplasty procedures (e.g., 532 nm), or vice versa. Typically, the radiation source further comprises a switch, configured to switch the treatment beams between a first optical path, which includes the wavelength converter, and a second optical path, which does not include the wavelength converter.

Alternatively or additionally, in such embodiments, optical unit 30 may further comprise one or more illumination sources 60 comprising, for example, one or more LEDs, such as white-light or infrared LEDs. For example, the optical unit may comprise a ring of LEDs surrounding opening 58. In such embodiments, controller 44 may cause illumination sources 60 to intermittently flash light at the eye during a trabeculoplasty procedure, as described in International Patent Application Publication WO/2020/008323, whose disclosure is incorporated herein by reference. This flashing may facilitate the imaging performed by the camera, and, by virtue of the brightness of the flashing, may further help constrict the pupil of the eye. (For ease of illustration, the electrical connection between controller 44 and illumination sources 60 is not shown explicitly in FIG. 2.) In some embodiments, illumination sources 60 are coupled to front face 33, as shown in FIG. 2.

As shown in FIG. 1, in some embodiments—particularly those in which a trabeculoplasty, which generally requires that the entire limbus be visible, is performed—the optical unit is directed obliquely upward toward the eye while the eye gazes obliquely downward toward the optical unit, such that path 92 is oblique. For example, the path may be oriented at an angle θ of between five and twenty degrees with respect to the horizontal. Advantageously, this orientation reduces occlusion of the patient's eye by the patient's upper eyelid and associated anatomy.

In some embodiments, as shown in FIG. 1, the oblique orientation of path 92 is achieved by virtue of the optical unit being mounted on a wedge 40, which is mounted on the XYZ stage unit. In other words, the optical unit is mounted onto the XYZ stage unit via wedge 40. (Wedge 40 is omitted from FIG. 2.)

In some embodiments, at least some of the functionality of controller 44, as described herein, is implemented in hardware, e.g., using one or more fixed-function or general-purpose integrated circuits, Application-Specific Integrated Circuits (ASICs), and/or Field-Programmable Gate Arrays (FPGAs). Alternatively or additionally, controller 44 may perform at least some of the functionality described herein by executing software and/or firmware code. For example, controller 44 may be embodied as a programmed processor comprising, for example, a central processing unit (CPU) and/or a Graphics Processing Unit (GPU). Program code, including software programs, and/or data may be loaded for execution and processing by the CPU and/or GPU. The program code and/or data may be downloaded to the controller in electronic form, over a network, for example. Alternatively or additionally, the program code and/or data may be provided and/or stored on non-transitory tangible media, such as magnetic, optical, or electronic memory. Such program code and/or data, when provided to the controller, produce a machine or special-purpose computer, configured to perform the tasks described herein.

In some embodiments, the controller comprises a system on module (SOM), such as the DART-MX8M by Variscite of Lod, Israel.

Defining the Treatment Zone

Figure 3:
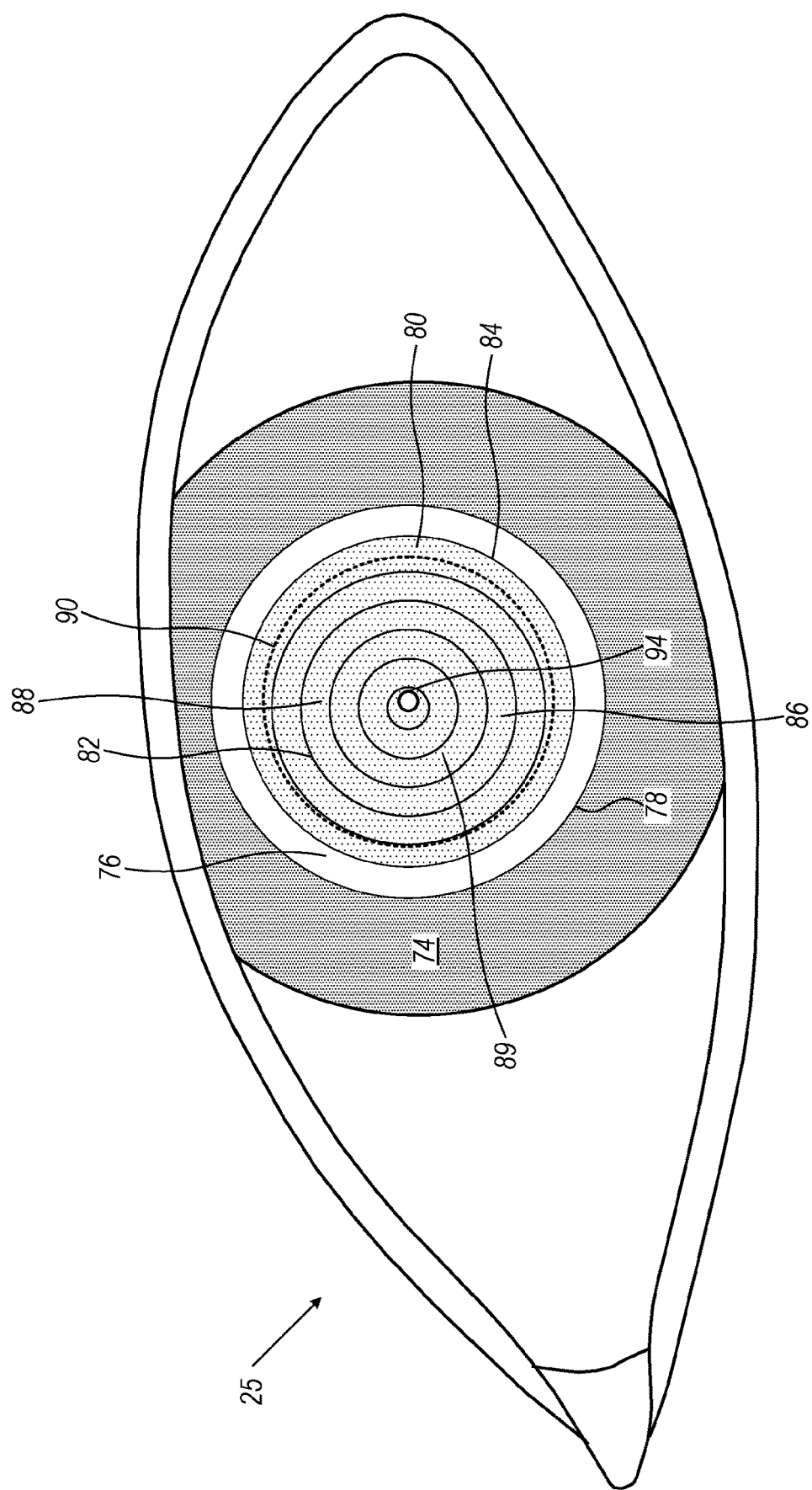
FIG. 3 is a schematic illustration of a method for defining a treatment zone, in accordance with some embodiments of the present invention.

Reference is now made to FIG. 3, which is a schematic illustration of a method for defining a treatment zone, in accordance with some embodiments of the present invention.

FIG. 3 shows eye 25 at the start of the capsulotomy procedure. In particular, FIG. 3 shows the anterior capsule 76 of the eye lying within the edge 78 of the iris 74 of the eye. An opening 84 has been formed in anterior capsule 76, so as to allow the natural lens of the eye to be removed (e.g., via phacoemulsification) and a prosthetic intraocular lens (IOL) 80 to be inserted. Behind IOL 80 lies an opacified posterior capsule 86 of the eye, on which the capsulotomy procedure is to be performed.

Typically, IOL 80 includes an elliptical optic 89 connected to curved filaments, or "haptics," that anchor the IOL in place. For example, optic 89 may be circular, having a diameter of between 6 and 14 mm. Although IOL 80 is generally transparent, in some cases, as shown in FIG. 3, one or more features of IOL 80 (in particular, optic 89 of the IOL) may be visible behind opening 84. For example, in some cases, optic 89 includes a Fresnel lens including multiple lens zones, and concentric circles 82, which demarcate the lens zones, are visible.

At the start of the capsulotomy procedure, controller 44 (FIG. 2) defines a treatment zone 88, demarcated in the present figures by a boundary 90, on posterior capsule 86. Typically, treatment zone 88 is elliptical, e.g., circular.

For example, based on at least one initial image of the eye acquired by camera 54 (FIG. 2), the controller may identify opening 84 in anterior capsule 76, e.g., by applying any suitable pattern-matching and/or edge-detection techniques to the initial image. Subsequently, the controller may define the treatment zone such that the treatment zone lies entirely behind the opening. For example, the controller may offset boundary 90 a predefined distance (e.g., 0.1-1 mm) inward from the perimeter of opening 84. As an extra safety precaution, the controller may further identify edge 78 of iris 74 based on the initial image, and verify that the treatment zone lies entirely within edge 78.

Alternatively, based on the initial image of the eye, the controller may identify one or more features of IOL 80, e.g., by applying any suitable pattern-matching and/or edge-detection techniques to the initial image. In response to the features, the controller may calculate an estimated position of the IOL, and then define the treatment zone in response to the estimated position. In particular, the controller may define the position and size of the treatment zone such that, even if the entire treatment zone were to be opened, the IOL would not fall through the opening. As an extra safety precaution, the controller may further verify that the treatment zone lies entirely within edge 78, and/or verify that the treatment zone lies entirely behind opening 84.

For example, prior to the procedure, a user may input, to the controller, relevant features of the IOL, such as the dimensions of, and/or number of lens zones belonging to, optic 89. Subsequently, based on the input and in response to identifying one or more circles 82, the controller may calculate the position of the center of the optic. In response thereto, the controller may center the treatment zone at the center of the optic, and/or offset boundary 90 a predefined distance (e.g., 0.5-1 mm) inward from the perimeter of the optic, e.g., per guidelines specified in the relevant medical literature.

Alternatively, the controller may define the treatment zone by offsetting boundary 90 a predefined distance (e.g., up to 1 mm) inward from edge 78, without necessarily identifying opening 84 or any features of IOL 80.

Typically, subsequently to defining the treatment zone, the controller overlays boundary 90, which demarcates the treatment zone, on the initial image of the eye, and displays the image with the overlaid boundary on monitor 42 (FIG. 1). The user may then adjust the treatment zone, e.g., by using a mouse to drag one or more points on boundary 90, prior to approving the treatment zone.

In other embodiments, the controller defines the treatment zone in response to input from the user, without necessarily performing any of the image processing described above.

For example, the user may input the desired center and radius of the treatment zone, and/or drag points on boundary 90 as described above.

Forming the Opening

Subsequently to defining treatment zone 88, the controller forms an opening in capsule 86 by irradiating multiple target regions 94 within the treatment zone in an iterative process. During each iteration of the process, the controller acquires an image of at least part of the capsule, designates one of the target regions 94 based on the acquired image, and causes radiation source 48 (FIG. 2) to irradiate the designated target region. For example, FIG. 3 shows an initial target region at the center of treatment zone 88, which the controller may designate and then irradiate during the first iteration of the process.

Figure 4:
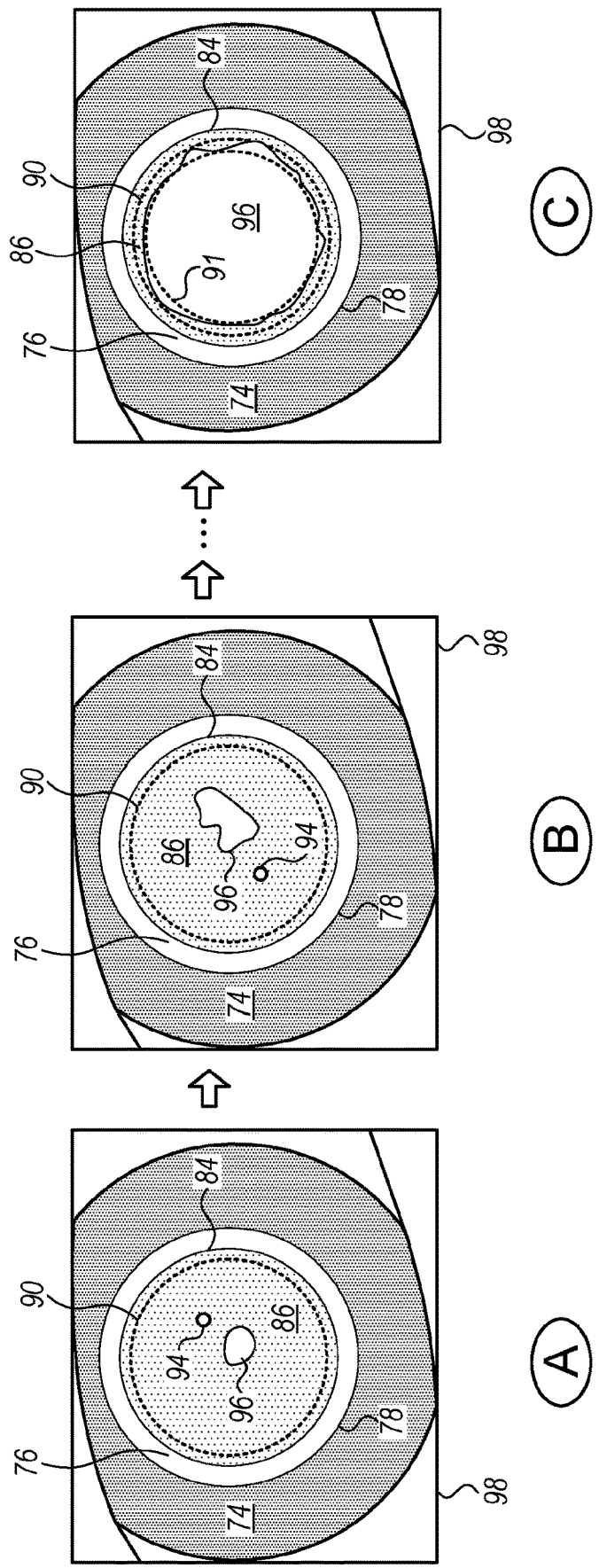
FIG. 4 is a schematic illustration of the formation of an opening in a capsule, in accordance with some embodiments of the present invention.

For further details, reference is now made to FIG. 4, which is a schematic illustration of the formation of an opening 96 in capsule 86, in accordance with some embodiments of the present invention.

Section A of FIG. 4 shows an image 98 of the eye following the initialization of opening 96, which is performed by irradiating the first designated target region 94 shown in FIG. 3. Based on the image, the controller designates a second target region 94, e.g., as further described below with reference to FIG. 5.

Section B of FIG. 4 shows another image 98 following the irradiation of the second target region, which expands opening 96. Based on the image, the controller designates a third target region 94.

Section C of FIG. 4 shows another image 98 following a number of further iterations in which target regions 94 are irradiated. Based on such an image, the controller may decide to refrain from designating any further target regions, thus terminating the iterative process.

For example, the controller may define a target boundary 91 for the opening, e.g., by placing target boundary 91 at a predefined offset (e.g., 0.01-1 mm) inward from boundary 90 of the treatment zone. Subsequently, the controller may terminate the process in response to ascertaining that the opening reaches a predefined threshold percentage (e.g., 90%-100%) of target boundary 91. (In such embodiments, prior to the first treatment beam, target boundary 91 may be overlaid on the initial image of the eye and the user may then adjust the target boundary, as described above for boundary 90 with reference to FIG. 3.) Alternatively (e.g., if the pupil of the eye is relatively small), the controller may terminate the process in response to ascertaining that the opening reaches a predefined threshold percentage (e.g., 90%-100%) of boundary 90 of the treatment zone.

Figure 5:
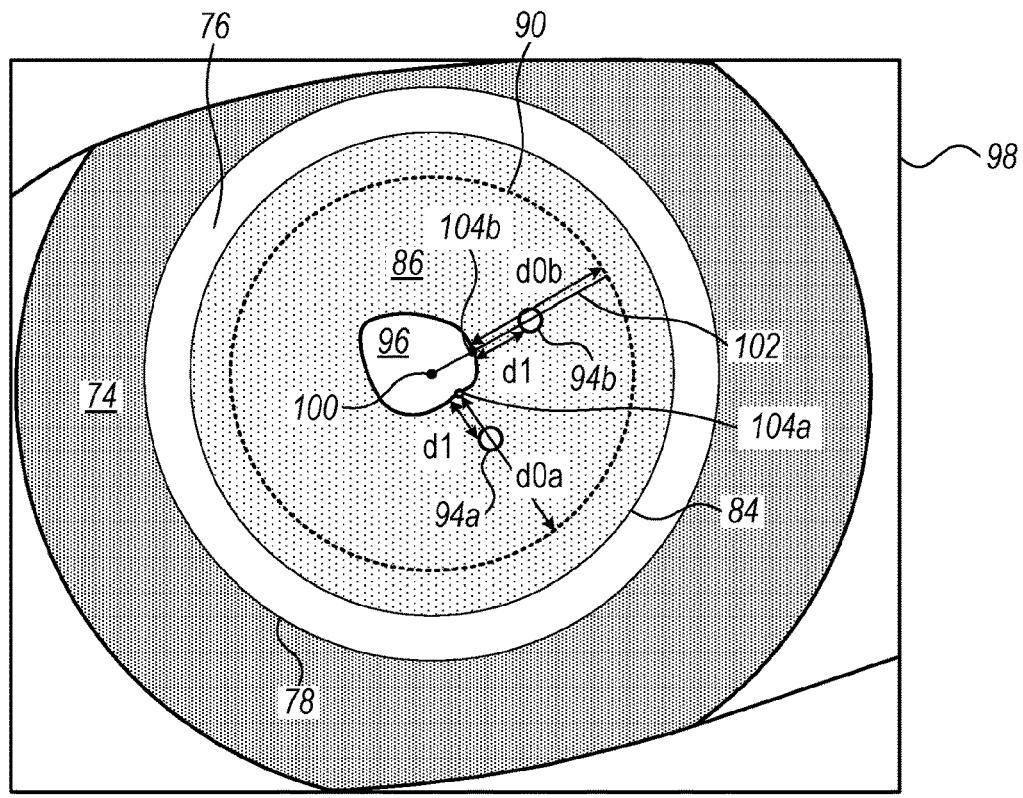
FIGS. 5-6 are schematic illustrations of techniques for designating target regions, in accordance with some embodiments of the present invention.

Reference is now made to FIG. 5, which is a schematic illustration of a technique for designating target regions 94, in accordance with some embodiments of the present invention.

FIG. 5 shows the scenario generally shown in Sections A-B of FIG. 4, in which opening 96 is being formed. In this scenario, in some cases, the controller designates the next target region by performing the following technique.

First, based on image 98, the controller identifies a portion of the perimeter of the opening that is farther from boundary 90 than are other portions of the perimeter.

For example, for multiple points 104a along the perimeter, the controller may calculate the shortest distance d0a between point 104a and boundary 90, i.e., the length of the shortest line between point 104a and boundary 90. Subsequently, the controller may identify the point 104a for which d0a is a maximum.

Alternatively, for multiple angles, the controller may calculate the distance d0b between (i) the point 104b at which a line 102 radiating from the center 100 of the treatment zone at the angle intersects the perimeter of opening 96, and (ii) the point at which line 102 intersects boundary 90. Subsequently, the controller may identify the point 104b for which d0b is a maximum.

Next, the controller designates target region 94 at a predefined distance d1 from the identified portion of the perimeter. For example, subsequently to identifying a point 104a as described above, the controller may designate a target region 94a lying on the shortest line between the identified point and boundary 90 at a distance of d1 from the identified point 104a Similarly, subsequently to identifying a point 104b as described above, the controller may designate a target region 94b lying on the line 102 joining the identified point to boundary 90, at a distance d1 from the identified point 104b.

Figure 6:
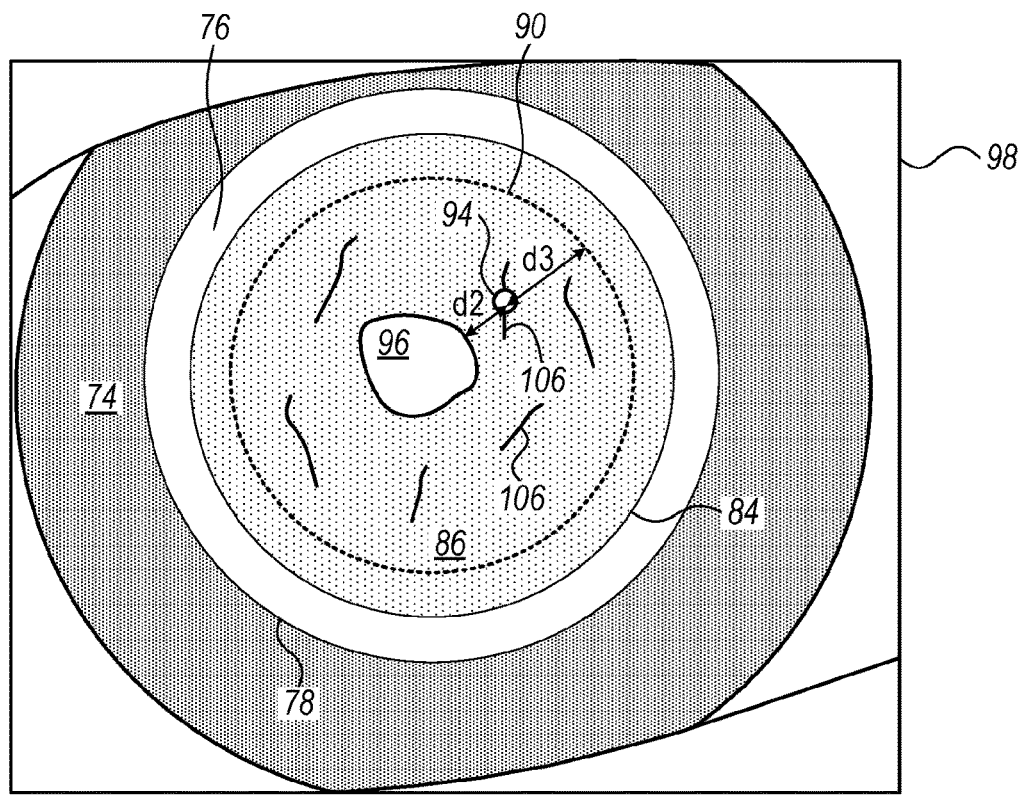

Reference is now made to FIG. 6, which is a schematic illustration of another technique for designating target region 94, in accordance with some embodiments of the present invention.

In some cases, at least one fold 106 in the tissue of the capsule lies within the treatment zone. In such cases, the controller may identify fold 106, e.g., by applying an edge-detection algorithm, a line-detection algorithm, or any other suitable image-processing algorithm to image 98. Subsequently, in response to identifying the fold, the controller may designate target region 94 such that the target region overlaps the fold.

For example, for each of the identified folds, the controller may calculate two distances: (i) the distance d2 between the center of the fold and the nearest point on the perimeter of the opening, and (ii) the distance d3 between the center of the fold and the nearest point on boundary 90. The controller may then identify a set of "targetable" folds for which d2 is within a predefined range of distances (e.g., 0.2-2 mm, such as 0.5-1 mm). Subsequently, the controller may select the targetable fold for which d3 is a maximum, and then place target region 94 at the center of the selected fold. Alternatively, if there are no targetable folds, the controller may instead use the technique of FIG. 5 to designate the target region.

Figure 7:
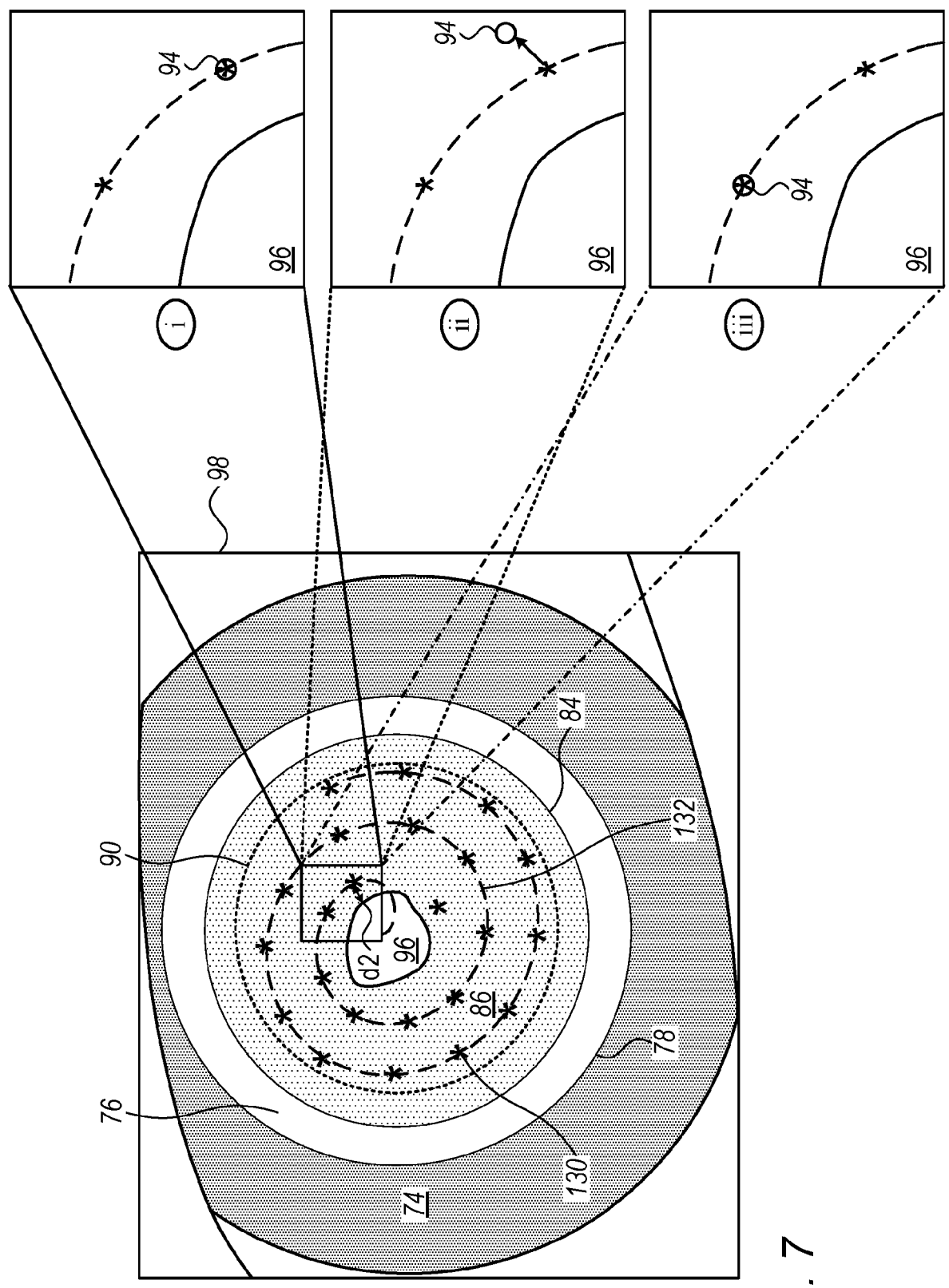
FIG. 7 is a schematic illustration of a technique for designating target regions based on a predesignated sequence of tentative target regions, in accordance with some embodiments of the present invention.

Reference is now made to FIG. 7, which is a schematic illustration of a technique for designating target regions based on a predesignated sequence of tentative target regions, in accordance with some embodiments of the present invention.

In some embodiments, prior to irradiating the capsule (and subsequently to the definition of the treatment zone), a sequence of tentative target regions 130 is designated. For example, the controller may display an image of the capsule to the user, and the user may then manually designate the sequence by clicking a mouse over each portion of the image at which a tentative target region 130 is desired. Alternatively, the controller may designate the sequence and display the sequence to the user, and the user may then approve the sequence after shifting, adding, or deleting any number of tentative target regions 130.

Typically, the sequence generally follows a geometric pattern. For example, the tentative target regions may be arranged in a spiral 132, which spirals outward from the center of the treatment zone, or in multiple crossed lines that define an asterisk. Parts of the sequence may deviate from the pattern slightly, e.g., so as to allow one or more tentative target regions 130 to overlap folds 106 (FIG. 6).

In such embodiments, when forming opening 96, the controller iterates through the sequence of tentative target regions 130. For each of the tentative target regions, the controller either (i) designates the tentative target region as the next target region 94, i.e., approves the tentative target region for irradiation, as illustrated in the top-right inset portion of FIG. 7, (ii) designates the next target region by applying an offset (typically away from the perimeter of opening 96) to the location of the tentative target region, as illustrated in the middle-right inset portion of FIG. 7, or (iii) designates the following tentative target region as the next target region, as illustrated in the bottom-right inset portion of FIG. 7.

In particular, for each tentative target region, the controller ascertains whether the distance d2 between the tentative target region and the perimeter of opening 96 is greater than a predefined threshold distance (e.g., 0.2-0.9 mm). If d2 is greater than the predefined threshold distance, the tentative target region is designated as the target region 94. Otherwise, the controller either applies the offset or designates the following tentative target region.

Notwithstanding the examples shown in FIGS. 4-7, it is noted that opening 96 need not necessarily be initialized at the center of the treatment zone. For example, when sweeping across the capsule in a cross or asterisk pattern, the first target region in each line of the cross or asterisk may be designated near the edge of the treatment zone.

Example Iterative Process

Figure 8:
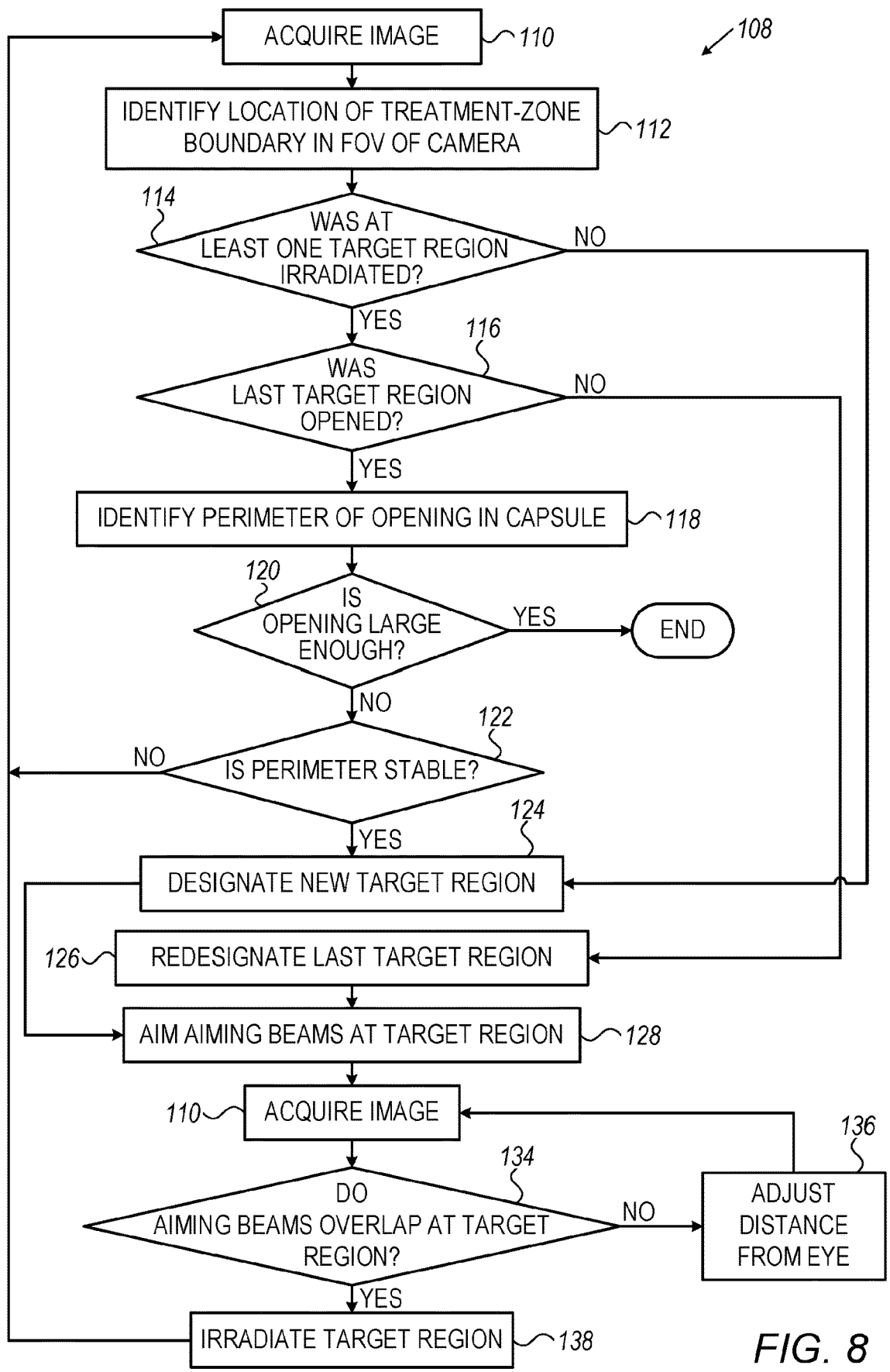
FIG. 8 is a flow diagram for an example iterative process for forming an opening in a capsule of an eye, in accordance with some embodiments of the present invention.

Reference is now made to FIG. 8, which is a flow diagram for an example iterative process 108 for forming an opening in a capsule of an eye, in accordance with some embodiments of the present invention. Iterative process 108 may be performed by the controller subsequently to defining the treatment zone, e.g., as described above with reference to FIG. 3.

Each iteration of process 108 begins with an imaging step 110, at which the controller, using camera 54 (FIG. 2), acquires an image of at least part of the capsule. Subsequently to imaging step 110, the controller, at a location-identifying step 112, identifies the location of boundary 90 (FIG. 3) of the treatment zone in the field of view (FOV) of the camera, by repeating whichever image processing was used previously to define the treatment zone. (The location of the treatment-zone boundary in the FOV may change throughout the procedure, due to movement of the eye.)

For example, if the treatment zone was defined by placing boundary 90 at a predefined distance from the perimeter of opening 84 (FIG. 3), the controller may identify the perimeter of opening 84 in the latest acquired image, and then identify the location of the treatment-zone boundary at the predefined distance therefrom. For embodiments in which target boundary 91 (FIG. 4) is defined, the controller may also identify the location of boundary 91 in the FOV of the camera.

Subsequently, at a checking step 114, the controller checks whether at least one target region was already irradiated (i.e., whether at least one iteration was already performed). If not, the controller performs a target-designating step 124, described below. Otherwise, the controller checks, at another checking step 116, whether the last-designated (and irradiated) target region was opened. In other words, based on the acquired image, the controller checks whether tissue of the capsule is present at the last-designated target region.

Typically, checking step 116 comprises two sub-steps. In the first sub-step, the controller identifies the location of the last target region based on the location of boundary 90. For example, based on the location of boundary 90, the controller may calculate any shift in the location of the center of the treatment zone, and then apply the same shift to the location of the last target region. Thus, for example, assuming that (i) the last target region was centered at (x0,y0) with the center of the treatment zone being at (0,0), and (ii) the center of the treatment zone is now at (dx,dy), the controller may identify (x0+dx,y0+dy) as the new location of the last target region. Subsequently, in the second sub-step, the controller computes the change in pixel value between the last target region in the current image and the last target region in the last image, and compares this change to a predefined threshold.

If the last target region was not opened (i.e., if the controller identifies capsular tissue at the last target region), the controller, at a target-redesignating step 126, redesignates the last target region. In some embodiments, the controller may also increase, by a predefined increment, the energy with which the target region is subsequently irradiated. (In such embodiments, typically, the energy may be increased multiple times by the predefined increment up to a predefined maximum energy, after which, if the target region is still not opened, process 108 is aborted.)

Alternatively, if the last target region was opened, the controller, at a perimeter-identifying step 118, identifies the perimeter of opening 96 (FIG. 4), e.g., using any suitable edge-detection algorithm. Subsequently, at a size-checking step 120, the controller checks whether the opening is large enough, e.g., by checking whether the opening reaches target boundary 91 as described above with reference to FIG. 4. If yes, process 108 ends. Otherwise, the controller proceeds to a stability-checking step 122.

At stability-checking step 122, the controller checks the stability of the perimeter of the opening by comparing the current location of the perimeter relative to the treatment-zone boundary, and shape of the perimeter, to the last location and shape. In response to ascertaining that the perimeter is stable, the controller proceeds to target-designating step 124. Alternatively, in response to ascertaining that the perimeter is not stable—i.e., that the opening is still expanding as a result of previous irradiation—the controller refrains from designating a new target region, and returns to imaging step 110.

At target-designating step 124, the controller designates a new target region. For example, the controller may first check for any targetable folds, as described above with reference to FIG. 6. If a targetable fold is found, the controller may target the fold, as further described above with reference to FIG. 6. Otherwise, the controller may designate a target region as described above with reference to FIG. 5 or FIG. 7.

Subsequently to performing target-designating step 124 or target-redesignating step 126, the controller, at an aiming step 128, aims aiming beams 53 (FIG. 2) at the designated target region. Subsequently, the controller acquires another image of the capsule at imaging step 110. The controller then checks, at a checking step 134, whether the aiming beams overlap one another at the designated target region. If not, the controller, at a distance-adjusting step 136, adjusts the distance of optical unit 30 from the eye, e.g., by communicating appropriate control signals to motors 34 (FIG. 2). Alternatively or additionally, the controller may adjust the position of at least one optic in the optical unit, such as galvo mirrors 50 or focusing module 72 (FIG. 2). The controller then acquires another image of the capsule, and repeats checking step 134. In this manner, the distance of the optical unit from the eye, and/or the position of the optic, may be iteratively adjusted by the controller. Alternatively, the distance of the optical unit from the eye may be manually adjusted by the user.

Upon the controller (or the user) ascertaining that the aiming beams overlap one another, the controller causes radiation source 48 (FIG. 2) to irradiate the designated target region, at an irradiating step 138. The controller then begins another iteration of process 108.

In some embodiments, the aiming beams are shaped to define different respective portions of a predefined composite pattern, such that the predefined composite pattern is formed on the capsule only when the aiming beams overlap one another. Examples of such patterns are described, for example, in International Patent Application Publication WO/2020/008323, whose disclosure is incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A system, comprising:
a radiation source; and
a controller, configured to:
define a treatment zone on a capsule of an eye of a subject, and
subsequently to defining the treatment zone, form an opening in the capsule by irradiating multiple target regions within the treatment zone in an iterative process that includes, during each one of multiple iterations of the process:
acquiring an image of at least part of the capsule,
based on the acquired image, designating one of the target regions on the at least part of the capsule, and
causing the radiation source to irradiate the designated target region.

2. The system according to claim 1, wherein the capsule is a posterior capsule.

3. The system according to claim 2, wherein the controller is configured to define the treatment zone by:
based on at least one initial image of the eye, identifying an anterior-capsule opening in an anterior capsule of the eye, and
defining the treatment zone such that the treatment zone lies entirely behind the anterior-capsule opening.

4. The system according to claim 1, wherein the controller is configured to define the treatment zone by:
based on at least one initial image of the eye, identifying an edge of an iris of the eye, and
defining the treatment zone such that the treatment zone lies entirely within the edge.

5. The system according to claim 1, wherein the controller is configured to define the treatment zone by:
based on at least one initial image of the eye, identifying one or more features of a prosthetic intraocular lens (IOL) in the eye,
in response to the features, calculating an estimated position of the IOL, and
defining the treatment zone in response to the estimated position.

6. The system according to claim 1, wherein, during at least one of the iterations, designating the target region includes:
based on the acquired image, identifying tissue of the capsule at a last-designated one of the target regions, and
in response to identifying the tissue, redesignating the last-designated one of the target regions.

7. The system according to claim 1, wherein, during at least one of the iterations, designating the target region includes:
based on the acquired image, identifying a portion of a perimeter of the opening that is farther from a boundary of the treatment zone than are other portions of the perimeter, and
designating the target region at a predefined distance from the identified portion of the perimeter.

8. The system according to claim 1, wherein, during at least one of the iterations, designating the target region includes:
based on the image, identifying a fold within the treatment zone, and
in response to identifying the fold, designating the target region such that the target region overlaps the fold.

9. The system according to claim 1, wherein, during at least one of the iterations, designating the target region includes:
based on the acquired image, ascertaining that a perimeter of the opening is stable, and
in response to the ascertaining, designating the target region.

10. The system according to claim 1,
wherein the controller is configured to form the opening subsequently to a designation of a sequence of tentative target regions, and
wherein, during at least one of the iterations, designating the target region includes:
based on the acquired image, ascertaining that a distance between a next one of the tentative target regions and a perimeter of the opening is greater than a predefined threshold distance, and
in response to ascertaining that the distance is greater than the predefined threshold distance, designating, as the target region, the next one of the tentative target regions.

11. The system according to claim 10, wherein, during at least one other one of the iterations, designating the target region includes:
based on the acquired image, ascertaining that the distance is not greater than the predefined threshold distance, and
in response to ascertaining that the distance is not greater than the predefined threshold distance, designating, as the target region, the tentative target region following the next one of the tentative target regions.

12. The system according to claim 10, wherein, during at least one other one of the iterations, designating the target region includes:
based on the acquired image, ascertaining that the distance is not greater than the predefined threshold distance, and
in response to ascertaining that the distance is not greater than the predefined threshold distance, designating the target region by applying an offset to a location of the next one of the tentative target regions.

13. The system according to claim 1, wherein the controller is further configured to:
define a target boundary on the capsule, and
terminate the iterative process in response to ascertaining that the opening reaches a predefined threshold percentage of the target boundary.

14. The system according to claim 13, wherein the controller is configured to define the target boundary by placing the target boundary at a predefined offset inward from a boundary of the treatment zone.

15. A method, comprising:
defining a treatment zone on a capsule of an eye of a subject; and
subsequently to defining the treatment zone, forming an opening in the capsule by irradiating multiple target regions within the treatment zone in an iterative process that includes, during each one of multiple iterations of the process:
acquiring an image of at least part of the capsule,
based on the acquired image, designating one of the target regions on the at least part of the capsule, and
causing a radiation source to irradiate the designated target region.

16. The method according to claim 15, wherein the capsule is a posterior capsule.

17. The method according to claim 16, wherein defining the treatment zone comprises:
based on at least one initial image of the eye, identifying an anterior-capsule opening in an anterior capsule of the eye; and
defining the treatment zone such that the treatment zone lies entirely behind the anterior-capsule opening.

18. The method according to claim 15, wherein defining the treatment zone comprises:
based on at least one initial image of the eye, identifying an edge of an iris of the eye; and
defining the treatment zone such that the treatment zone lies entirely within the edge.

19. The method according to claim 15, wherein defining the treatment zone comprises:
based on at least one initial image of the eye, identifying one or more features of a prosthetic intraocular lens (IOL) in the eye;
in response to the features, calculating an estimated position of the IOL; and
defining the treatment zone in response to the estimated position.

20. The method according to claim 15, wherein, during at least one of the iterations, designating the target region includes:
based on the acquired image, identifying tissue of the capsule at a last-designated one of the target regions, and
in response to identifying the tissue, redesignating the last-designated one of the target regions.

21. The method according to claim 15, wherein, during at least one of the iterations, designating the target region includes:
based on the acquired image, identifying a portion of a perimeter of the opening that is farther from a boundary of the treatment zone than are other portions of the perimeter, and
designating the target region at a predefined distance from the identified portion of the perimeter.

22. The method according to claim 15, wherein, during at least one of the iterations, designating the target region includes:
based on the image, identifying a fold within the treatment zone, and
in response to identifying the fold, designating the target region such that the target region overlaps the fold.

23. The method according to claim 15, wherein, during at least one of the iterations, designating the target region includes:
based on the acquired image, ascertaining that a perimeter of the opening is stable, and
in response to the ascertaining, designating the target region.

24. The method according to claim 15,
wherein forming the opening comprises forming the opening subsequently to a designation of a sequence of tentative target regions, and
wherein, during at least one of the iterations, designating the target region includes:
based on the acquired image, ascertaining that a distance between a next one of the tentative target regions and a perimeter of the opening is greater than a predefined threshold distance, and
in response to ascertaining that the distance is greater than the predefined threshold distance, designating, as the target region, the next one of the tentative target regions.

25. The method according to claim 24, wherein, during at least one other one of the iterations, designating the target region includes:
based on the acquired image, ascertaining that the distance is not greater than the predefined threshold distance, and
in response to ascertaining that the distance is not greater than the predefined threshold distance, designating, as the target region, the tentative target region following the next one of the tentative target regions.

26. The method according to claim 24, wherein, during at least one other one of the iterations, designating the target region includes:
based on the acquired image, ascertaining that the distance is not greater than the predefined threshold distance, and
in response to ascertaining that the distance is not greater than the predefined threshold distance, designating the target region by applying an offset to a location of the next one of the tentative target regions.

27. The method according to claim 15, further comprising:
defining a target boundary on the capsule; and
terminating the iterative process in response to ascertaining that the opening reaches a predefined threshold percentage of the target boundary.

28. The method according to claim 27, wherein defining the target boundary comprises defining the target boundary by placing the target boundary at a predefined offset inward from a boundary of the treatment zone.

29. A computer software product comprising a tangible non-transitory computer-readable medium in which program instructions are stored, which instructions, when read by a controller, cause the controller to:
define a treatment zone on a capsule of an eye of a subject, and
subsequently to defining the treatment zone, form an opening in the capsule by irradiating multiple target regions within the treatment zone in an iterative process that includes, during each one of multiple iterations of the process:
acquiring an image of at least part of the capsule,
based on the acquired image, designating one of the target regions on the at least part of the capsule, and
causing a radiation source to irradiate the designated target region.

* * * * *